United States Patent [19]

Baker et al.

[11] Patent Number: 5,441,955
[45] Date of Patent: Aug. 15, 1995

[54] INDOLO[2,1-B]QUINAZOLINE-6,12-DIONE ANTIBACTERIAL COMPOUNDS AND METHODS OF USE THEREOF

[75] Inventors: William R. Baker, Bellevue, Wash.; Lester A. Mitscher, Lawrence, Kans.

[73] Assignee: PathoGenesis Corporation, Seattle, Wash.

[21] Appl. No.: 154,784

[22] Filed: Nov. 19, 1993

[51] Int. Cl.⁶ .................. A61K 31/495; A61K 31/53; C07D 487/22; C07D 491/22
[52] U.S. Cl. .................. 514/250; 514/253; 514/254; 514/257; 544/246; 544/247
[58] Field of Search ............ 544/246, 247; 514/250, 514/253, 254, 257

[56] References Cited

FOREIGN PATENT DOCUMENTS

4114990A1 11/1992 Germany .

OTHER PUBLICATIONS

Mitscher, L. A. et al., "Antimicrobial Agents From Higher Plants. New Synthesis and Bioactivity of Tryptanthrin (Indolo-[2,1-b]-Quinazolin-6,12-Dione) and Its Analogues," *Heterocycles* 15(2):1017–1021 (1981).
Mitscher, L. A. et al., "A Modern Look At Folkoric Use of Anti-Infective Agents," *J. Natural Products* 50(6):1025–1040 (1987).
Fiedler, E. et al., "Stoffwechselprodukte von Mikroorganismen," *Arch. Microbiol.* 107:249–256 (1976).
Kikumoto, R. and Kobayashi, T., "The Reactions of Oxindoles and Isatin with Nitrobenzyl Chlorides," *Tetrahedron* 22:3337–3343 (1966).
Hooper, M. and Pitkethyl, W. N., "2-Arylmethylideneindolin-3-ones: Stereochemistry and Reduction and Sodium Borohydride," *J. Chem. Soc. Perkin I* 1607–1613 (1972).
Staskun, B. and Wolfe, J., "New Approach to the indolo[2,1-b]quinazoline ring system by cyclization of 3-(o-chlorophenyl)-2-methyl-4(3H)-quinazoline and its m-isomer. Synthesis of the antibiotic tryptanthrin," *S. Afr. J. Chem.* 45(1):5–7 (1992).
Eguchi, S. et al., "Short-Step Synthesis of Rutecarpine and Tryptanthrin via Intramolecular aza-Wittig Reaction," *Heterocycles* 33(1):153–156 (1992).
Bergman, J. et al., "The Structure and Properties of Some Indolic Constituents in *Couroupita Guianesis* Aubl.," *Tetrahedron* 41(14):2879–2881 (1985).
Honda, G. and Tabata, M., "Isolation of Antifungal Principle Tryptanthrin, from Strobilanthes Cusia O. Kuntze," *Planta medica, J. Med. Plant Res.* 36:85–86 (1979).

(List continued on next page.)

*Primary Examiner*—Mukund J. Shah
*Assistant Examiner*—Matthew V. Grumbling
*Attorney, Agent, or Firm*—Christensen, O'Connor, Johnson and Kindness

[57] ABSTRACT

Methods, compounds and compositions are provided form inhibiting the growth of pathogenic mycobacteria in vitro and of treatment of pathogenic mycobacterial infections in vivo using indolo[2,1-b]quinazoline-6,12-dione compounds of the formula (I):

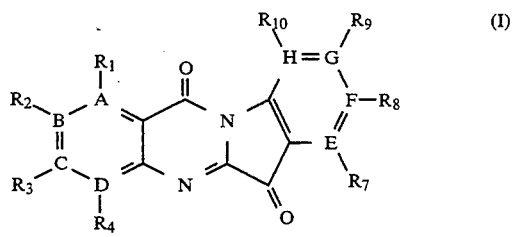

wherein A, B, C, D, E, F, G and H are independently selected from carbon and nitrogen, or A and B or C and D can be taken together to be nitrogen or sulfur, and the pharmaceutically acceptable salts thereof. The methods, compounds and compositons are particularly useful for inhibiting the growth of *Mycobacterium tuberculosis*, and may be used alone, or in combination with other anti-*Mycobacterium tuberculosis* agents, such as isoniazid, rifampin, pyrazinamide, rifabutin, streptomycin and ciprofloxacin, to provide new agents for the treatment of tuberculosis, including multidrug-resistant tuberculosis (MDRTB).

19 Claims, 3 Drawing Sheets

OTHER PUBLICATIONS

Honda, G. et al., "Isolation of an Antidermatophytic, Tryptanthrin, from Indigo Plants, *Polygonum tinctorium* and *Isatis tinctoria*," *Planta medica, J. Med. Plant Res.* 38:275-276 (1980).

Honda, G. et al., "The Antimicrobial Specificity of Tryptanthrin," *Planta medica, J. Med. Plant Res.* 37:172-174 (1979).

Bergman et al., "Reduction and Stereochemical Studies through N.M.R. and X-Ray Techniques Indolo[2,1-b]-quinazolines," *J. Chem. Soc. Perkin Trans. I* 519-527 (1987).

Schindler, F. and Zahner, H., "Stoffwechselprodukte von Mikroorganismen," *Arch. Mikrobiol.* 79:187-203 (1971).

Brufani, M. et al., "The Structure of Tryptanthrin," *Experientia Specialia* 27(11):1249-1250 (1971).

Bergman, J. et al., "The Structure of Some Indolic Constituents in *Couroupita Guaianensis* Aubl.," *Tetrahedron Lett.* 30:2625-2626 (1977).

Bird, C. W., "The Structure of Methylisatoid," *Tetrahedron* 19:901-904 (1963).

Bergman, J. and Tilstam, U., "Structure Determination of Candidine, A Violet Indolic Constituent from Culture Solutions of *Candida Lipolytica*," *Tetrahedron* 41(14):2883-2884 (1985).

Akazome, M. et al., "Transition–Metal Complex-Catalyzed Reductive N-Heterocyclization: Synthesis of 4(3H)-Quinazolinone Derivatives from N-(2-Nitrobenzoyl)amides," *J. Org. Chem.* 58:310-312 (1993).

International Search Report in corresponding international application PCT/US94/13259.

Chemical Abstracts, No. 46155b, 76(9):374 (1972); Brufani et al., "Metabolic products of microorganisms. 92. The structure of tryptanthrin," *Experientia*, 27(110):1249-1250 (1971).

Chemical Abstracts No. 56406y, 76(11):213 (1972); Schindler et al., "Metabolic products of microorganisms. 91. Tryptanthrin, a tryptophan-derived antibiotic from Candida lipolytica," *Archiv. Mikrobiologica*, 79(3):187-203 (1971).

Chemical Abstracts, No. 18927x, 85(3):497 (1976); Fiedler et al., "Metabolic products of microorganisms. Part 156. Synthesis and biosynthesis of substituted tryptanthrins," *Archiv. Microbiologica*, 107(3):249-256 (1976).

Chemical Abstracts, No. 87332k, 91(11):415 (1979); Honda et al., "Isolation of antifungal principle tryptanthrin from Strobilanthes cusia O. Kuntze," *Planta Medica*, 36(1):85-86 (1979).

Chemical Abstracts, No. 211856w, 92(25):315 (1980); Honda et al., "Isolation of an antidermatophytic tryptanthrin, from the indigo plants, Plygonum tinctorium and Isatis tinctoria," *Planta Medica*, 38(3):275-276 (1980).

Chemical Abstracts, No. 85563c, 120(1):944-945 (1994); Baiocchi et al., "Synthesis and antimicrobial activity of some new indolo[2,1-b]quinazolin-6(12H)ones," *Farmaco*, 48(4), (1993).

Chemical Abstracts, No. 12501k, 100(2):355 (1984); Li et al., "Studies on the antifungal constituent of Qing Dai (Isatis indigotica)," *Zhongcaoyao*, 14(10):440-441 (1983).

Chemical Abstracts, No. 192264z, 94(23):656 (1981); Mitscher et al., "Antimicrobial agents from higher plants. New synthesis and bioactivity of tryptanthrin (indo[2,1-b]quinazoline-6,12-dione)," *Heterocycles*, 15(2):1017-1021 (1981).

Chemical Abstracts, No. 7463b, see column 7462h through 7463c, 59(7) (30 Sep. 1963); Bird, "Structure of methylisatoid," *Tetrahedron*, 19(6):901-904 (1963).

Chemical Abstracts, No. 1831g, 58(2) (1963); Sareen, "Anticonvulsant drugs based on the neurochemistry of seizures," *Indian J. Physiol. Pharmacol.*, 6:87-94 (1962).

Chemical Abstracts, No. 9422b, see columns 9422a through 9423d, 55(10) (1961); Butler et al., "Cyclic amidines. XIV. Derivatives of 7H-5,6a,12-triazebenz-[a]anthracene," *J. Chem. Soc.*, 4970-4976 (1960).

INDOLO[2,1-B]QUINAZOLINE-6,12-DIONE ANTIBACTERIAL COMPOUNDS AND METHODS OF USE THEREOF

FIELD OF THE INVENTION

The present invention relates to new indolo[2,1-b]quinazoline-6,12-dione derivatives which are useful in killing mycobacteria, to antimicrobial compositions containing the compounds and to the use of the compounds and compositions, alone or in combination with other antimicrobial agents, in the treatment of pathogenic mycobacterial infections.

BACKGROUND OF THE INVENTION

After a decline in rates of infection over several decades, a disturbing increase in the incidence of tuberculosis (TB) is occurring. Because TB is highly contagious it poses a profound threat to public health. TB bacteria are easily passed from person to person in airborne droplets formed when a person with active TB sneezes or coughs.

Even more alarming has been the rise of multidrug-resistant tuberculosis (MDRTB). Prior to 1984, about 10 percent of TB bacteria isolated from patients in the United States were resistant to even a single antibacterial drug. In 1984, 52 percent of patients were infected with *Mycobacterium tuberculosis* (also referred to as *tubercle bacilli*) resistant to at least one drug, and 32 percent were resistant to one or more drugs. Outbreaks of MDRTB have been reported in 13 states. Ten percent of the recorded MDRTB cases to date have occurred in previously healthy people whose mortality rate—70 to 90 percent—has been nearly the same as that of immunosuppressed persons with MDRTB (Snider and Roper, 1992).

The United States Centers for Disease Control (CDC) has released preliminary results of a joint study with the New York State Health Department showing that cases of drug-resistant TB have more than doubled since 1984. CDC data from the first quarter of 1991 show that many of these drug-resistant strains are resistant to both of the frontline TB drugs, rifampin and isoniazid. Outbreaks of MDRTB have occurred in hospitals in Miami and New York City, as well as in the New York State prison system. In one hospital in New York City, the median interval between diagnosis of MDRTB and death was only four weeks. Additional clusters of MDRTB were reported to the CDC in 1990 and 1991 from Mississippi, Missouri, and Michigan.

There are five frontline drugs known to be highly effective against *Mycobacterium tuberculosis* and five second-line drugs that can be used when resistance to one or more of the frontline drugs is detected. Ironically, in the United States, until April 1992, there were shortages of antituberculosis drugs, some of which are crucially needed when resistance to the frontline drugs rifampin and isoniazid is present. These shortages had occurred because several pharmaceutical companies had ceased production of these drugs.

Because of its persistence in the body, the tubercle bacillus is a notoriously difficult pathogen to control. Although bacille Calmette-Guerin (BCG) vaccine protects against severe tuberculosis meningitis and disseminated TB in children, its efficacy against pulmonary TB in adults has varied widely in different parts of the world. Treatment of conventional TB is effective, but expensive, requiring daily treatment with multiple drugs for a minimum of six months. There is a common tendency among TB patients to stop taking their drugs when the drugs begin to have their beneficial effect or to take the medications only intermittently. When this happens, relapses are frequent and very often are caused by drug-resistant *tubercle bacilli* that have survived the initial course of treatment. The emergence of drug-resistant *M. tuberculosis* is in many ways an index of individual compliance with antituberculosis chemotherapy and of the inability of the health care infrastructure to ensure adequate treatment. Many public health agencies that once could play key roles in this process have had their budgets cut drastically in recent years and hence are unable to perform this crucial service.

MDRTB is extraordinarily difficult to treat, and a majority of patients do not respond to therapy. Total treatment costs for an individual with MDRTB can be as much as ten times the cost of traditional treatment; the cost of the treatment drugs alone can be as much as 21 times as great.

The preferred treatment for classical TB consists of isoniazid, rifampin, and pyrazinamide. For patients whose *tubercle bacilli* are thought to be resistant to isoniazid, a fourth drug, ethambutol, is commonly added to the regimen until drug susceptibility results are known. Isolates of *tubercle bacilli* resistant to both isoniazid and rifampin, now representing about 20 percent in some cities, require specialized treatment with additional medications, which may include streptomycin and ciprofloxacin for almost two years.

The *tubercle bacillus* is a slow-growing organism. Three to six weeks are needed to grow the bacteria in the clinical laboratory, and an additional three to six weeks are needed to screen for antibiotic resistance. Such extended laboratory procedures can result in a delay in diagnosis, which means that patients with unrecognized drug-resistant TB may be treated ineffectively and remain infectious for a longer period. In HIV-positive individuals, MDRTB usually causes death within 4 to 16 weeks after being diagnosed, which is often before laboratory tests on drug susceptibility and resistance can be completed.

There is no evidence that mutation rates in *M. tuberculosis* organisms have increased or that increased virulence is to blame for the recent deadly outbreaks of TB. It is likely that drug-resistant forms of tuberculosis arose because of patient noncompliance with the 6- to 12-month regimen of antibiotics required to treat TB. Ineffective treatment regimens also play a role in the rising incidence of TB. To address noncompliance, some states with high TB rates are considering approaches to outreach, such as expanding directly observed therapy (DOT); others may reestablish inpatient facilities similar to the TB sanatoria of the first half of this century. Standard treatment regimens for TB have also been updated. Instead of taking two or three antibiotics, TB patients now take four. Still, as noted earlier, the current shortages of antituberculosis drugs in the United States have made even standard treatment difficult.

Tryptanthrin (indolo-[2,1-b]quinazolin-6,12-dione) is a material that is produced naturally in some plant species, and has been produced synthetically by a base catalyzed condensation of isatin and isatoic anhydride (L. A. Mitscher et al., "Antimicrobial Agents From Higher Plants. New Synthesis and Bioactivity of Tryptanthrin (Indolo-[2,1-b]-quinazolin-6,12-dione) and its Analogs," *Heterocycles* 15(2):1017–1021 (1981)). Tryptanthrin and some of its analogs have been shown to exhibit some antimicrobial activity against various bacterial and yeast species, including *Staphylococcus aureus, Klebsiella pneumoniae*, nonpathogenic *Mycobacterium smegmatis* and *Candida albicans*, although activity has been found to be highly variable depending on individual species and substitution of the parent compound (see Mitscher et al., supra). To date, however, there has been no indication in the prior art that tryptanthrin exhibits antimicrobial activity against pathogenic mycobacteria, that various derivatives of this compound may exhibit enhanced activity, or that various derivatives may be highly useful in the treatment of MDRTB.

SUMMARY OF THE INVENTION

It has now been surprisingly discovered that pathogenic mycobacteria can be controlled in vitro or in vivo by certain indolo[2,1-b]quinazoline-6,12-dione derivatives. Accordingly, the present invention provides methods of inhibiting the growth of pathogenic mycobacteria in vitro and of treatment of pathogenic mycobacterial infections in vivo using indolo[2,1-b]quinazoline-6,12-dione compounds of the formula (I):

(I)

[Chemical structure]

wherein A, B, C, D, E, F, G and H are independently selected from carbon and nitrogen, or A and B and/or C and D can be taken together to be sulfur, oxygen or nitrogen with the proviso that not more than three of A, B, C, D, E, F, G and H are other than carbon;

wherein $R_1$ through $R_4$, $R_8$ and $R_{10}$ are independently selected from the group consisting of hydrogen, halogen, loweralkyl, cycloalkyl, heterocycle, substituted heterocycle, amino, imino, haloloweralkyl, alkoxy, nitro, alkylsulfonyl, arylalkyl, arylalkylaryl, arylaryl, aryloxy, arylamino, acylamino, acyloxyamino, alkylaminoacylamino, alkylaminosulfonylamino, alkylamino, alkenylamino, dialkylamino, alkoxyalkylamino, alkoxyalkylheterocycle, mercaptoalkoxyalkyl, cyano, formyl, —$COOR_{11}$ where $R_{11}$ is hydrogen, loweralkyl, aryl, heterocycle, monosaccharide or disaccharide, and —$COONR_{12}R_{13}$ where $R_{12}$ and $R_{13}$ are independently selected from hydrogen, loweralkyl, aryl, heterocycle, saccharide, peptide and amino acid residues;

$R_7$ and $R_9$ are independently selected from hydrogen, halogen, loweralkyl, haloloweralkyl, cycloalkyl, heterocycle, substituted heterocycle and heterocyclicalkyl;

and the pharmaceutically acceptable salts thereof.

Presently particularly preferred and novel compounds of the invention are provided by the compounds of formula (I) having a backbone structure wherein D is nitrogen, and A–C and E–H are carbon.

In a presently preferred embodiment for the treatment of tuberculosis, the methods and compounds of the invention may be employed alone, or in combination with other anti-*Mycobacterium tuberculosis* agents, such as isoniazid, rifampin, pyrazinamide, rifabutin, streptomycin and ciprofloxacin, to provide new agents for the treatment of tuberculosis, including MDRTB.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

In the accompanying drawings.

DETAILED DESCRIPTION OF THE PREFERRED EMBODIMENT

Figure 1:
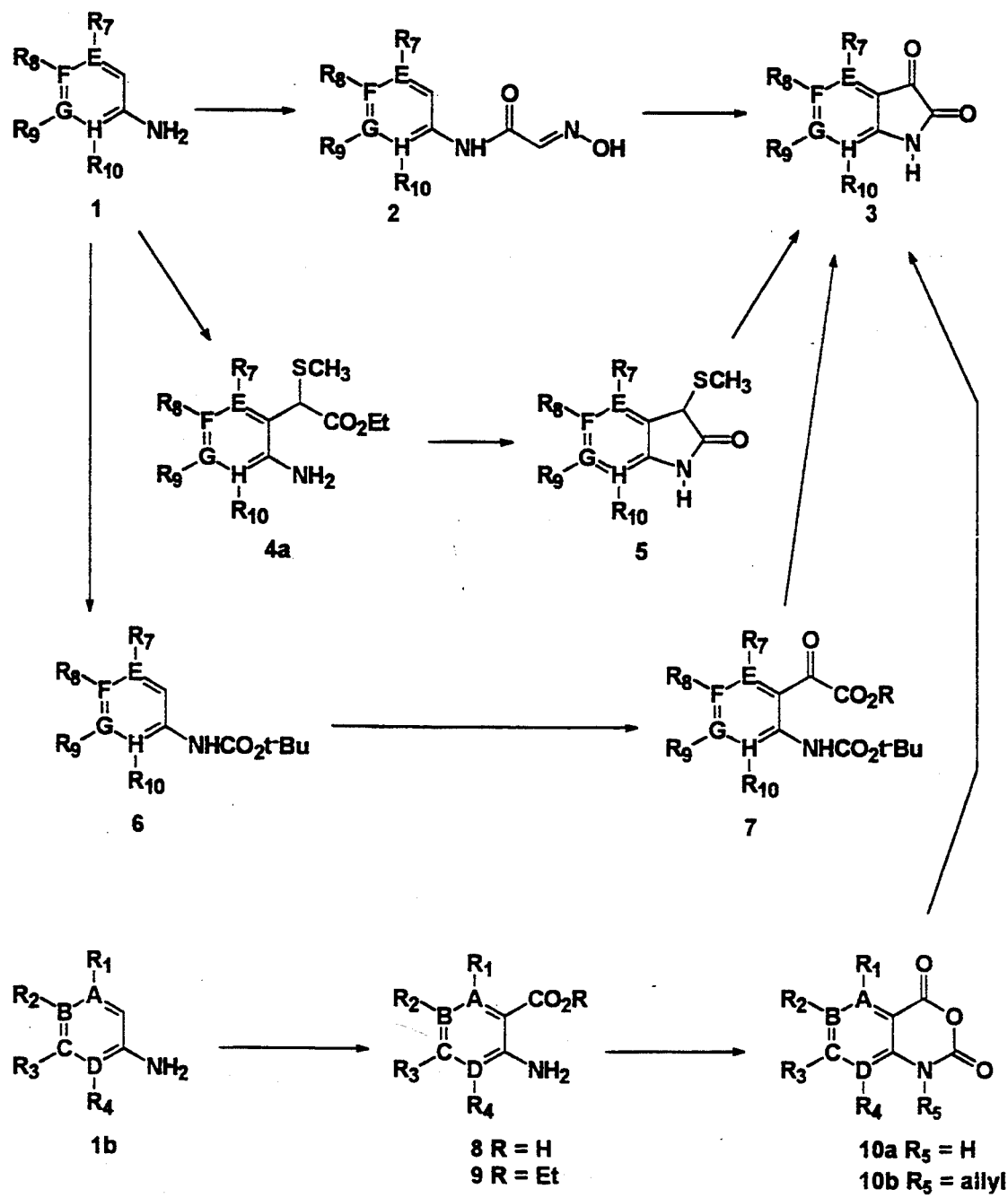
FIG. 1 is a schematic representation of alternative synthesis pathways of intermediate isatin and isatoic anhydride compounds of the invention.

In accordance with the present invention, methods are provided for control of pathogenic mycobacteria, either in vitro or in vivo. Thus, in one aspect the present invention provides a method of inhibiting the growth of *Mycobacterium sp.* in vitro comprising contacting the *Mycobacterium sp.* with a growth inhibitory amount of a indolo[2,1-b]quinazoline-6,12-dione compound of the formula (I):

(I)

[Chemical structure]

wherein A, B, C, D, E, F, G and H are independently selected from carbon and nitrogen, or A and B or C and D can be taken together to be nitrogen or sulfur, with the proviso that not more than three of A, B, C, D, R, F, G and H are other than carbon;

$R_1$ through $R_4$, $R_8$ and $R_{10}$ are independently selected from the group consisting of hydrogen, halogen, loweralkyl, cycloalkyl, heterocycle, substituted heterocycle, amino, imino, haloloweralkyl, alkoxy, nitro, alkylsulfonyl, arylalkyl, arylalkylaryl, arylaryl, aryloxy, arylamino, acylamino, acyloxyamino, alkylaminoacylamino, alkylaminosulfonylamino, alkylamino, alkenylamino, dialkylamino, alkoxyalkylamino, alkoxyalkylheterocycle, mercaptoalkoxyalkyl, cyano, formyl, —$COOR_{11}$ where $R_{11}$ is hydrogen, loweralkyl, aryl, heterocycle, monosaccharide or disaccharide, and —$COONR_{12}R_{13}$ where $R_{12}$ and $R_{13}$ are independently selected from hydrogen, loweralkyl, aryl, heterocycle, saccharide, peptide and amino acid residues; and $R_7$ and $R_9$ are independently selected from hydrogen, halogen, loweralkyl, haloloweralkyl, cycloalkyl, heterocycle, substituted heterocycle and heterocyclicalkyl;

or $R_1$ through $R_{10}$ are absent when the ring atom to which they would otherwise be bonded is sulfur or double-bonded nitrogen;

and the pharmaceutically acceptable salts thereof.

In another aspect, the present invention provides methods of treating human or animal subjects suffering from a pathogenic mycobacterial infection, e.g., tuberculosis, whether of sensitive-strain or multi-drug resistant strain (MDRTB) origin. Thus, the present invention provides a method of treating a human or animal subject in need of such treatment comprising administering to the subject a therapeutically effective amount of a indolo[2,1-b]quinazoline-6,12-dione compound of formula (I), above, either alone or in combination with other antibacterial or antifungal agents.

In another aspect, the present invention provides new antimicrobial indolo[2,1-b]quinazoline-6,12-dione compounds of the formula:

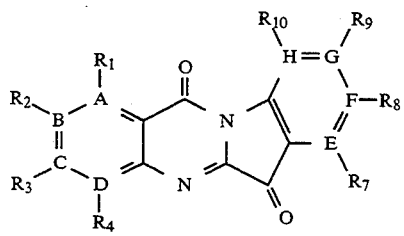

wherein A, B, C, D, E, F, G and H are independently selected from carbon and nitrogen, or A and B or C and D can be taken together to be nitrogen or sulfur, with the proviso that at least one of A, B, C, D, E, F, G and H must be other than carbon;

wherein $R_1$ through $R_4$, $R_8$ and $R_{10}$ are independently selected from the group consisting of hydrogen, halogen, loweralkyl, cycloalkyl, heterocycle, substituted heterocycle, amino, imino, haloloweralkyl, alkoxy, nitro, alkylsulfonyl, arylalkyl, arylalkylaryl, arylaryl, aryloxy, arylamino, acylamino, acyloxyamino, alkylaminoacylamino, alkylaminosulfonylamino, alkylamino, alkenylamino, dialkylamino, alkoxyalkylamino, alkoxyalkylheterocycle, mercaptoalkoxyalkyl, cyano, formyl, —$COOR_{11}$ where $R_{11}$ is hydrogen, loweralkyl, aryl, heterocycle, monosaccharide or disaccharide, and —$COONR_{12}R_{13}$ where $R_{12}$ and $R_{13}$ are independently selected from hydrogen, loweralkyl, aryl, heterocycle, saccharide, peptide and amino acid residues;

$R_7$ and $R_9$ are independently selected from hydrogen, halogen, loweralkyl, haloloweralkyl, cycloalkyl, heterocycle, substituted heterocycle and heterocyclicalkyl;

or $R_1$ through $R_{10}$ are absent when the ring atom to which they would otherwise be bonded is sulfur or double-bonded nitrogen;

and the pharmaceutically acceptable salts thereof.

As used above and elsewhere herein the following terms have the meanings defined below:

The term "pathogenic mycobacteria" refers to mycobacterial organisms which do not normally reside in a human or animal host, and which are capable of causing a disease state in the host. Representative examples of pathogenic mycobacteria include, for example, *Mycobacteria tuberculosis*, *Mycobacteria leprae*, *Mycobacteria avium* complex, and the like, including multidrug-resistant *M. tuberculosis* strains.

The term "acylamino" means an acyl (CO—) radical to which an amino group is appended.

The term "loweralkyl" as used herein refers to branched or straight chain alkyl groups comprising one to ten carbon atoms, including, e.g., methyl, ethyl, propyl, isopropyl, n-butyl, t-butyl, neopentyl and the like.

The term "alkoxy" as used herein refers to RO— wherein R is loweralkyl as defined above. Representative examples of lower alkoxy groups include methoxy, ethoxy, t-butoxy and the like.

The term "alkenyl" as used herein refers to a branched or straight chain groups comprising two to twenty carbon atoms which also comprises one or more carbon-carbon double bonds. Representative alkenyl groups include 2-propenyl (i.e., allyl), 3-methyl-2-butenyl, 3,7-dimethyl-2,6-octadienyl, 4,8-dimethyl-3,7-nonadienyl, 3,7,11-trimethyl-2,6,10-dodecatrienyl and the like.

The term "alkynyl" as used herein refers to a branched or straight chain comprising two to twenty carbon atoms which also comprises one or more carbon-carbon triple bonds. Representative alkynyl groups include ethynyl, 2-propynyl (propargyl), 1-propynyl and the like.

The term "aryl" as used herein refers to a phenyl or a $C_9$- or $C_{10}$-bicyclic carbocyclic ring system having one or more aromatic rings, including naphthyl, tetrahydronaphthyl, indanyl, indenyl and the like. Aryl groups can be unsubstituted or substituted with one, two or three substituents independently selected from loweralkyl, haloalkyl, alkoxy and halo.

The term "arylalkyl" as used herein refers to a loweralkyl radical to which is appended an aryl group. Representative arylalkyl groups include benzyl, phenylethyl, hydroxybenzyl, fluorobenzyl, fluorophenylethyl and the like.

The term "arylalkylaryl" as used herein refers to an arylalkyl group as previously defined appended to an aryl group. Representative arylalkylaryl groups include 4-benzylphenyl, 3-benzylphenyl, 4-phenethylphenyl and the like.

The term "arylaryl" as used herein refers to an aryl group as previously defined which is appended to an aryl group. Representative arylaryl groups include biphenyl, 4-(1-naphthyl)phenyl, 4-(2-naphthyl)phenyl and the like.

The term "aryloxy" as used herein refers to RO— wherein R is an aryl group. Representative arylalkoxy group include benzyloxy, phenylethoxy and the like.

The term "arylalkoxy" as used herein refers to a lower alkoxy radical to which is appended an aryl group. Representative arylalkoxy group include benzyloxy, phenylethoxy and the like.

The term "aryloxyaryl" as used herein refers to an aryl radical to which is appended an aryloxy group. Representative aryloxyaryl groups include 4-phenoxyphenyl, 3-phenoxyphenyl, 4-phenoxy-1-naphthyl, 3-phenoxy-1-naphthyl and the like.

The term "aryloxyarylalkyl" as used herein refers to an arylalkyl radical to which is appended an aryloxy group. Representative aryloxyarylalkyl groups include 4-phenoxyphenylmethyl, 3-phenoxyphenylmethyl, 4-phenoxyphenylethyl, 3-phenoxyphenylethyl and the like.

The term "arylalkoxyaryl" as used herein refers to an aryl radical to which is appended an arylalkoxy group. Representative arylalkoxyaryl groups include 4-benzyloxyphenyl, 3-benzyloxyphenyl and the like.

The term "arylalkoxyarylalkyl" as used herein refers to an arylalkyl radical to which is appended an arylalkoxy group. Representative arylalkoxyarylalkyl groups include 4-benzyloxybenzyl, 3-benzyloxybenzyl and the like.

The term "cycloalkyl" as used herein refers to an alicyclic group comprising from 3 to 7 carbon atoms including, but not limited to, cyclopropyl, cyclobutyl, cyclopentyl, cyclohexyl and the like.

The term "cycloalkylalkyl" as used herein refers to a loweralkyl radical to which is appended a cycloalkyl group. Representative examples of cycloalkylalkyl include cyclopropylmethyl, cyclohexylmethyl, 2-(cyclopropyl)ethyl and the like.

The term "halogen" or "halo" as used herein refers to iodo, bromo, chloro or fluoro.

The term "haloalkyl" as used herein refers to a lower alkyl radical, as defined above, bearing at least one halogen substituent, for example, chloromethyl, fluoroethyl or trifluoromethyl and the like.

The term "heterocycle" as used herein refers to an aromatic ring system composed of 5 or 6 atoms selected from the heteroatoms nitrogen, oxygen, and sulfur. The heterocycle maybe composed of one or more heteroatoms that are either directly connected such as pyrazole or connected through carbon such as pyrimidine. Heterocycles can be substituted or unsubstituted with one, two or three substituents independently selected from amino, alkylamino, halogen, alkyl acylamino, loweralkyl aryl, alkoxy.

The term "substituted heterocycle" or "heterocyclic group" or heterocycle as used herein refers to any 3- or 4-membered ring containing a heteroatom selected from nitrogen, oxygen, and sulfur or a 5- or 6-membered ring containing from one to three heteroatoms selected from the group consisting of nitrogen, oxygen, or sulfur; wherein the 5-membered ring has 0-2 double bounds and the 6-membered ring has 0-3 double bounds; wherein the nitrogen and sulfur atom maybe optionally oxidized; wherein the nitrogen and sulfur heteroatoms maybe optionally quarternized; and including any bicyclic group in which any of the above heterocyclic rings is fused to a benzene ring or another 5- or 6-membered heterocyclic ring independently defined above. Heterocyclics in which nitrogen is the heteroatom are preferred. Fully saturated heterocyclics are also preferred. Preferred heterocycles include: diazapinyl, pyrryl, pyrrolinyl, pyrrolidinyl, pyrazolyl, pyrazolinyl, pyrazolidinyl, imidazoyl, imidazolinyl, imidazolidinyl, pyridyl, piperidinyl, pyrazinyl, piperazinyl, N-methyl piperazinyl, azetidinyl, N-methylazetidinyl, pyrimidinyl, pyridazinyl, oxazolyl, oxazolidinyl, isoxazolyl, isoazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, triazolyl and benzothienyl.

Heterocyclics can be unsubstituted or monosubstituted or disubstituted with substituents independently selected from hydroxy, halo, oxo (C=O), alkylimino (RN=, wherein R is a loweralkyl group), amino, alkylamino, dialkylamino, acylaminoalkyl, alkoxy, thioalkoxy, polyalkoxy, loweralkyl, cycloalkyl or haloalkyl. The most preferred heterocyclics include imidazolyl, pyridyl, piperazinyl, azetidinyl, thiazolyl, triazolyl and the following:

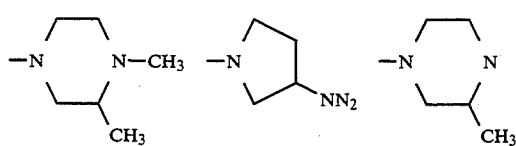

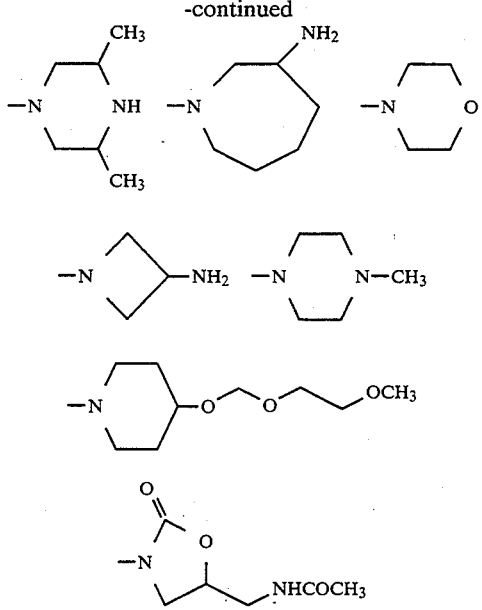

The compounds of the invention comprise asymmetrically substituted carbon atoms. Such asymmetrically substituted carbon atoms can result in the compounds of the invention comprising mixtures of stereoisomers at a particular asymmetrically substituted carbon atom or a single stereoisomer. As a result, racemic mixtures, mixtures of diastereomers, as well as single diastereomers of the compounds of the invention are included in the present invention. The terms "S" and "R" configuration, as used herein, are as defined by the IUPAC 1974 *Recommendations for Section E, Fundamental Stereochemistry, Pure Appl. Chem.* (1976) 45, 13–30. The terms α and β are employed for ring positions of cyclic compounds. The α-side of the reference plane is that side on which the preferred substituent lies at the lowered numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, as used herein, are as defined by the *Chemical Abstracts Index Guide—Appendix IV* (1987) paragraph 203.

Preferred compounds of the invention include compounds of the formula (II):

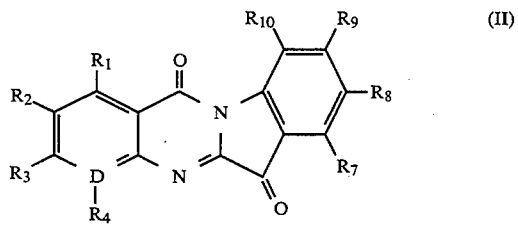

wherein D is carbon or nitrogen;

$R_1$ through $R_4$, $R_8$ and $R_{10}$ are independently selected from the group consisting of hydrogen, loweralkyl, heterocycle, substituted heterocycle, amino, halogen, nitro, alkylamino, dialkylamino, alkoxyalkylamino, and alkylheterocycle, provided that $R_4$ is absent when D is N; and $R_7$ and $R_9$ are independently selected from hydrogen, halogen, loweralkyl, cycloalkyl, heterocycle, substituted heterocycle and heterocyclicalkyl;

and the pharmaceutically acceptable salts thereof.

Even more preferred compounds of the invention include compounds of the formula (III):

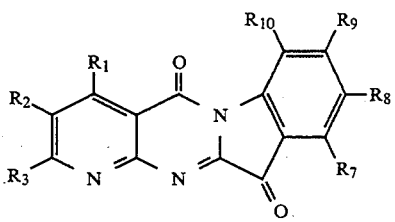

wherein $R_1$ through $R_3$, $R_8$ and $R_{10}$ are independently selected from the group consisting of hydrogen, loweralkyl, heterocycle, substituted heterocycle, amino, halogen, nitro, alkylamino, dialkylamino, alkoxyalkylamino, and alkylheterocycle;

$R_7$ and $R_9$ are independently selected from hydrogen, halogen, loweralkyl, cycloalkyl, heterocycle, substituted heterocycle and heterocyclicalkyl;

and the pharmaceutically acceptable salts thereof.

The presently most preferred compounds of the invention include compounds of the formula (IV):

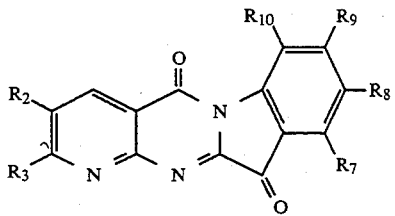

wherein $R_2$, $R_3$, $R_8$ and $R_{10}$ are independently selected from the group consisting of hydrogen, halogen, loweralkyl, heterocycle, and substituted heterocycle;

$R_7$ and $R_9$ are independently selected from hydrogen and halogen;

and the pharmaceutically acceptable salts thereof.

The present invention also relates to the processes for preparing the compounds of the invention and to the synthetic intermediates useful in such processes, as described in detail below.

In yet a further aspect of the present invention, pharmaceutical compositions are provided which comprise a compound of the present invention in combination with a pharmaceutically acceptable carrier.

Figure 2:
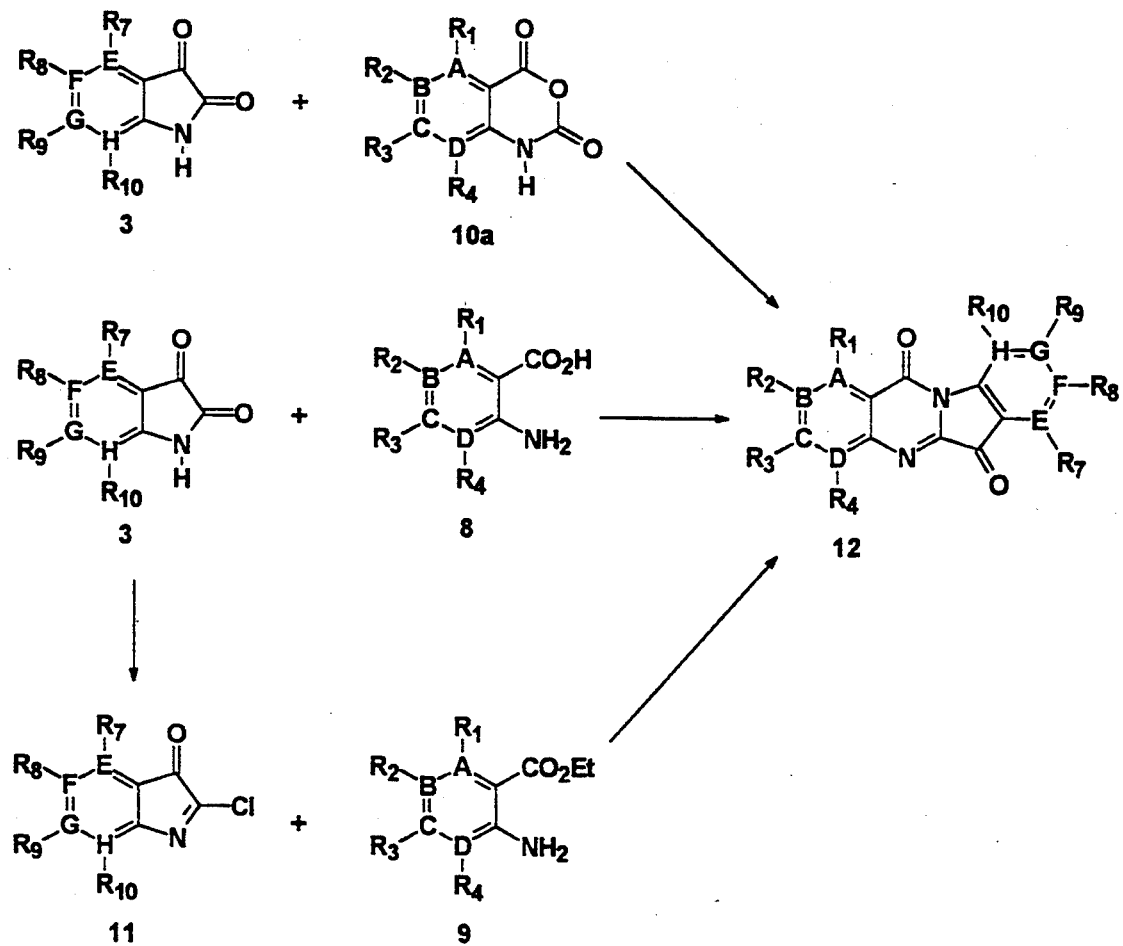
FIG. 2 is a schematic representation of alternative synthesis pathways of the indolo[2,1-b]quinazoline-6,12-dione compounds of the invention.
Figure 3:
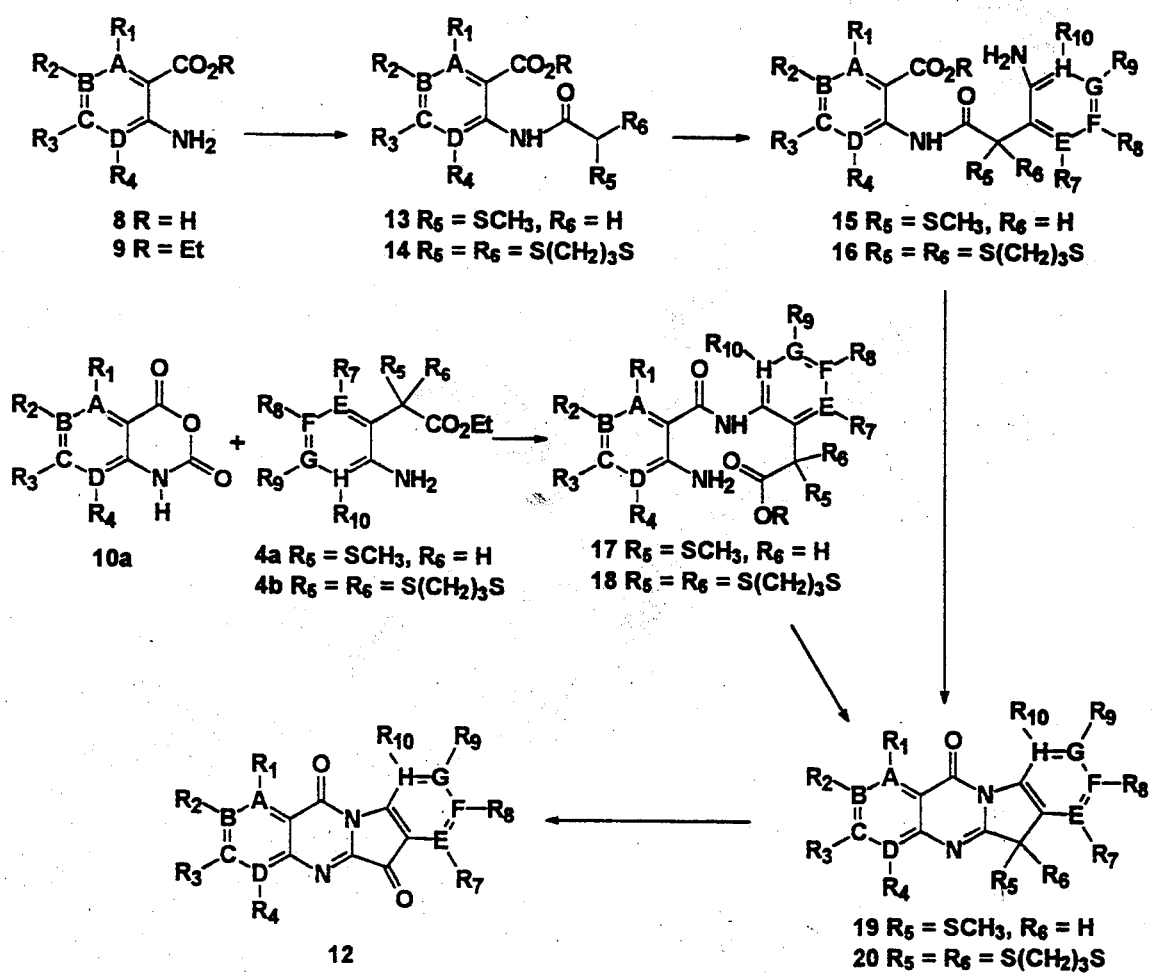
FIG. 3 is a schematic representation of an alternative synthesis pathway of compounds of the invention.

In general, the compounds of the invention can be prepared by the processes illustrated in Schemes I (FIG. 1), II (FIG. 2), and III (FIG. 3). According to the reaction Scheme I substituted isatin derivatives 3 are prepared by four methods. The first method involves reaction of substituted anilines with hydroxylamine and chloral hydrate in aqueous hydrochloric acid according to the procedure of T. Sandmeyer et al., *Helv. Chim. Acta.* 2:234 (1919) and C. S. Marvel et al., *Org. Syn. Coll.* 1:327 (1941) to give the anilides 2. Cyclization of anilides 2 to isatins 3 is effected by treating compound 2 in hot concentrated sulfuric acid. A second synthesis of isatins 3 from anilines 1 was accomplished using the procedures of Gassman et al. *J. Org. Chem.*, 42:1344 (1977). Thus, reaction of aniline 1 with t-butylhypochlorite at $-70°$ C. followed by ethyl thiomethylacetate, triethylamine and warming the reaction mixture to room temperature gave the anilino esters 4. Esters 4 were not isolated but were cyclized to the oxindoles 5 using aqueous hydrochloric acid. Oxindoles 5 were converted to isatins 3 by oxidation with N-chlorosuccinimide and mercuric oxide. A third method for the synthesis of isatins 3 involves the metalation of t-butyloxycarbonylanilines 6 with alkyllithium reagents (for example, n-butyllithium, sec-butyllithium, tert-butyllithium) in an inert and dry solvent such as tetrahydrofuran (THF), dimethoxyethane (DME), dioxane and the like. The resultant dianion is reacted with esters or amides of oxalic acid (for example, diethyl oxalate, ethyl oxalochloride, N-methyl, N-methoxy oxalamide, the half ester/amide, ethyl N-methyl, N-methoxy oxalamide) in the presence of a Lewis acid such as magnesium bromide, boron trifluoride, copper (I) iodide and the like to give the alpha ketoester 7. Deprotection of the Boc group and cyclization to isatins 3 is accomplished using HCl or trifluoroacetic acid in methanol, dichloromethane, dioxane, diethyl ether and the like. A fourth and final method for the preparation of isatins 3 involves the reaction of N-allyl isatoic anhydrides 10b with potassium cyanide according to the procedure of G. Coppola *J. Heterocyclic Chem.* 7:827 and 1501 (1979). The resulting N-allylisatins are reacted with palladium (O) then aqueous acid to give isatins 3. The required N-allyl isatoic anhydrides are prepared by reaction of isatoic anhydrides 10a with strong bases (for example, sodium hydride, potassium hydride or t-butoxide, lithium diisopropylamide and the like) in an inert solvent such as tetrahydrofuran, dimethylformamide, N-methylpyrrolidinone with allyl bromide at low temperature (for example, $-50°$ C. to ambient temperature). Isatoic anhydrides are prepared from either 2-aminocarboxylic acid derivatives 8 or isatins 3 (see G. Coppola, *Synthesis* 505–536, 1980, and references cited therein).

Referring now to FIG. 2, Scheme II illustrates the preparation of indolo[2,1-b]quinazoline derivatives from substituted isatin 3. Reaction of isatin 3 with a strong base such as sodium hydride, potassium hydride or t-butoxide, 1,8-diaza[5,4,1]bicycloundec-7-ene (DBU) and the like in an inert solvent (for example, tetrahydrofuran, dimethylformamide, N-methylpyrrolidinone or pyridine) and isatoic anhydride 10a in dimethylaminopyridine (DMAP) gives the indolo[2,1-b]quinazoline derivatives 12. A second synthesis of the indoloquinazolines 12 was accomplished by reaction of isatins 3 with 2-aminobenzoic acids or 2-aminopyridine carboxylic acids with a peptide coupling reagent, such as hydroxybenzotriazole (HOBT)/dicyclohexylcarbodiimide (DCC) or 2-[1H-benzotriazole-1-yl]-1,1,3,3,-tetramethyluronium hexaflurorphosphate (HBTU) and the like. The peptide coupling reaction may be conducted in a polar aprotic solvent (for example, dimethylformamide (DMF), N-methylpyrrolidone (NMP), tetrahydrofuran (THF) with a base such as 1,8-diaza[5,4,1]bicycloundec-7-ene (DBU), pyridine, N-methylmorpholine and the like. A third synthesis of compounds 12 may be obtained by the reaction of isatins 3 with iminoyl chlorides 11. Reaction of isatins 3 with chlorinating reagent (for example, phosphorus pentachloride, phosphorus oxychloride, thionyl chloride, oxalyl chloride and the like) give the isatin iminoyl chloride 11. Reaction of the iminoyl chloride 11 with the amino ester 9 in acetic acid, dichloroethane or tetrahydrofuran gives the indolo[2,1-b]quinazoline.

Referring now to FIG. 3, Scheme III illustrates two alternative methods for the preparation of indolo[2,1-b]quinazolines 12. The first method involves the reaction of ester 9 or acid 8 with either methylthioacetic acid or 1,3-dithiane-2-carboxylic acid and a coupling reagent (for example, DCC/HOBT/DMAP, carbonyldiimidazole (CDI) and the like) to give the amides 13 and 14, respectively (R=H or ethyl). Amides 13 and 14 are reacted with aniline 1 using the procedure described previously to afford compounds 15 and 16. In the case where R=ethyl, the ester is hydrolyzed using an alkaline bases such as sodium hydroxide, lithium hydroxide in water, aqueous ethanol, dioxane or tetrahydrofuran and the like. The resulting amino acids 15 and 16 are cyclized to give the indolo[2,1-b]quinazoline skeleton 19 and 20 using the procedure described by A. Singh et al. *Ind. J. Chem.* 7:881–883 (1969) (dicyclocarbodiimide (DCC) in benzene for 4–10 h at reflux temperature). The indolo[2,1-b]quinazoline derivatives 12 are obtained from 19 by oxidation with NCS/mercuric oxide and from 20 by dithiane hydrolysis (for example, the dithiane group is hydrolyzed using N-bromosuccinimide (NBS) in aqueous acetone (see E. Cain et al. *Tetrahedron Lett.* 1353 (1975)). Alternatively, amino ester 4a or 4b ($R_5$=H, $R_6$=SCH$_3$ or $R_5$=$R_6$=S(CH$_2$)$_3$S, prepared from aniline 1 and ethyl methylthioacetate and ethyl 1,3-dithiane-2-carboxylate, respectively) reacts with anhydride 10a using DMAP as a catalyst in an inert solvent (for example, tetrahydrofuran, dimethylformamide, N-methylpyrrolidinone and pyridine) to give the amides 17 and 18. The amino esters 17 and 18 are hydrolyzed as previously described to give the amino acids which are cyclized to indolo[2,1-b]quinazolines 19 and 20.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-napthalenesulfonate, oxalate, pamoate, pectinate, persulfate, 3-phenylproionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Basic addition salts can be prepared in situ during the final isolation and purification of the compounds of formula (I), or separately by reacting carboxylic acid moieties with a suitable base such as the hydroxide, carbonate or bicarbonate of a pharmaceutical acceptable metal cation or with ammonia, or an organic primary, secondary or tertiary amine. Pharmaceutical acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

The compounds of the invention are useful in vitro in inhibiting the growth of pathogenic mycobacteria, and in vivo in human and animal hosts for treating pathogenic mycobacterial infections, including tuberculosis. The compounds may be used alone or in compositions together with a pharmaceutically acceptable carrier.

Total daily dose administered to a host in single or divided doses may be in amounts, for example, from 0.001 to 1000 mg/kg body weight daily and more preferred from 1.0 to 30 mg/kg body weight daily. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in $\frac{1}{3}$-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any nontoxic, physiologically acceptable and metabolizable lipid capable of forming liposomes can be used. The present compositions in liposome form can contain, in addition a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W. (1976), p.33 et seq.

While the compounds of the invention can be administered as the sole active pharmaceutical agent, they can also be used in combination with one or more other agents used in the treatment of pathogenic mycobacterial infections. Representative agents useful in combination with the compounds of the invention for the treatment of *M. tuberculosis* include, for example, isoniazid, rifampin, pyrazinamide, ethambutol, rifabutin, streptomycin, ciprofloxacin and the like.

The above compounds to be employed in combination with the indolo[2,1-b]quinazoline-6,12-dione compounds of the invention will be used in therapeutic amounts as indicated in the Physicians' Desk Reference (PDR) 47th Edition (1993), which is incorporated herein by reference, or such therapeutically useful amounts as would be known to one of ordinary skill in the art.

The compounds of the invention and the other antiinfective agent can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions which are given at the same time or different times, or the therapeutic agents can be given as a single composition.

The foregoing may be better understood by reference to the following examples, which are provided for illustration and are not intended to limit the scope of the inventive concepts.

EXAMPLE 1

Preparation of 5,6-difluoroisatin and 4,5-difluoroisatin

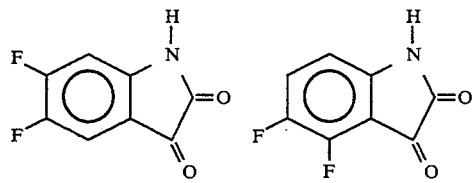

To a solution of 3,4-difluoroaniline (12.98 g, 0.100 mol) in 325 mL of methylene chloride at −65° C. was added a solution of t-butylhypochlorite (10.86 g, 0.100 mol) in 52 mL of methylene chloride. The mixture was stirred for 10 min. A solution of ethyl thiomethylacetate (13.49 g, 0.100 mol) in 65 mL of methylene chloride was added dropwise to the mixture and stirred at −65° C. for 1 h. Triethylamine (10.17 g, 0.100 mol) in 65 mL of methylene chloride was added and the reaction mixture was warmed to room temperature and stirred for 3 h. Water was added and the methylene chloride layer was separated and concentrated under reduced pressure to yield an oil. The resulting oil was diluted with 300 mL of diethyl ether and 80 mL of 2N HCl, and stirred for 24 h. A precipitate was formed, filtered and washed with 50 mL of diethyl ether to give a mixture of 5,6- and 4,5-difluoro-3-thiomethyloxindoles in 70% yield.

The crude oxindoles (11.64 g, 0.054 mol) were reacted with N-chlorosuccinimide (7.26 g, 0.05 mol) in 500 mL of chloroform at room temperature for 1 h. The reaction mixture was concentrated and the resulting residue was dissolved in 70 mL of THF. To this solution was added red mercury (II) oxide (11.78 g, 0.054 mol), boron trifluoride etherate (7.72 g, 0.05 mol), and 400 mL of aqueous 20% THF. The slurry was stirred for 3 h, diluted with 1000 mL of chloroform and filtered through celite. The resulting solids were washed with chloroform and the chloroform layer was separated and concentrated. Chromatography on silica gel eluting with 1% isopropyl alcohol:chloroform gave 5,6-difluoroisatin (Saul Kadin, U.S. Pat. No. 4,721,712) and 4,5-difluoroisatin in 31% and 4% yield, respectively. 4,5-Difluoroisatin: mp 140° C. (dec); $^1$H NMR (300 MHz, DMSO-$d_6$) δ 11.25 (s, 1H), 7.7 (dd, 1H), 6.7 (dd, 1H).

EXAMPLE 2

5,6,7-trifluoroisatin

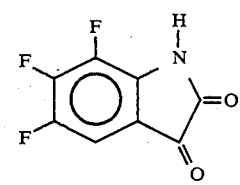

Using the procedure in Example 1 and substituting 2,3,4-trifluoroaniline for 3,4-difluoroaniline gave 5,6,7-trifluoro-3-methylthiooxindole in 51% yield: mp 177°–178.5° C.; $^1$H NMR (300 MHz, DMSO-$d_6$)δ 11.3 (s, 1H) 7.30–7.39 (m, 1H) 4.65 (s, 1H) 1.95 (s, 3H). 5,6,7-trifluoroisatin was obtained in an overall yield of 37.5%:

mp 192.8°–194.3° C.; $^1$H NMR (300 MHz, DMSO-d$_6$) δ 11.8 (s, 1H) 7.60–7.75 (m, 1H).

EXAMPLE 3

5,7-difluoroisatin

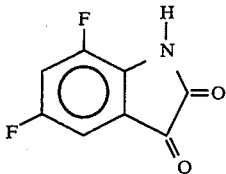

Using the procedure in Example 1 and substituting 2,4-difluoroaniline for 3,4-difluoroaniline gave 5,7-difluoro-3-methylthiooxindole in 57% yield: mp 150.7°–152.0° C.; $^1$H NMR (300 MHz, DMSO-d$_6$) δ 11.1 (s, 1H) 7.16–7.43 (m, 1H) 7.01–7.12 (m, 1H) 4.7 (s, 1H) 1.93 (s, 3H); MS (M+CH$_4$CN)$^+$ 257. 5,7-difluoroisatin was obtained in an overall yield of 39% yield: mp 188.5°–194° C.; $^1$H NMR (300 MHz, DMSO-d$_6$) δ 11.6 (s, 1H) 7.60–7.73 (m, 1H) 7.43–7.4 (m, 1H).

EXAMPLE 4

5-fluoro-6-(4-methylpiperazinyl)isatin

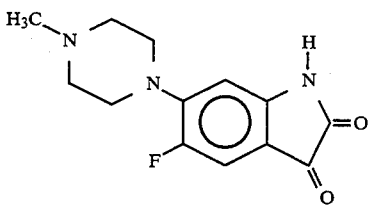

To a solution of 5,6-difluoroisatin (1.0 g, 5 mmol) in 50 mL of dimethyl sulfoxide was added N-methylpiperazine (5.47 g, 50 mmol). The mixture was stirred for 4 h at room temperature and the crude reaction mixture was diluted with ethyl acetate. The organic solution was washed with saturated sodium bicarbonate. The organic layers were separated and concentrated to give the title compound in 72% yield: mp 150° C. (dec); $^1$H NMR (300 MHz, DMSO-d$_6$)δ 10.8 (br s, 1H), 7.3 (d, 1H), 6.4 (d, 1H), 2.25 (s, 3H), 2.2 (m, 4H), 2.1 (m, 4H).

EXAMPLE 5

5-fluoro-6-(3-methyl-4-tertbutyloxycarbonyl piperazinyl)isatin

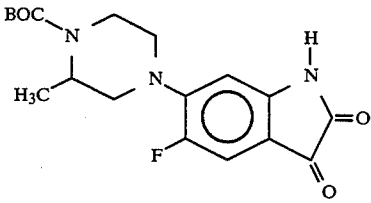

To a solution of 5-fluoro-6-(3-methylpiperazinyl)isatin (0.585 g, 2 mmol) in 30 mL of dry THF was added dropwise di-t-butyldicarbonate (0.727 g, 3 mmol) in 5 mL of THF. The mixture was stirred for 2 h at room temperature and the crude mixture was concentrated under reduced pressure. Chromatography of the residue on silica gel using methanol:chloroform as eluent gave the title compound in 69% yield: mp 160° C. (dec);
$^1$H NMR (300 MHz, CDCl$_3$) δ 8.8 (br s, 1H), 7.3 (s, 1H), 6.4 (d, 1H), 4.35 (br s, 1H), 4.0 (d, 1H), 3.65 (t, 2H), 3.3 (dt, 1H), 3.25 (dt, 1H), 3.1 (t, 1H), 1.5 (s, 9H), 1.3 (s, 3H).

EXAMPLE 6

5,7-difluoro-6-(4-methylpiperazinyl)isatin

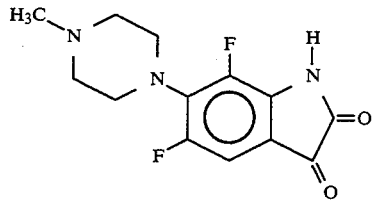

Using the procedure in Example 4 and substituting 5,6,7-trifluoroisatin for 5,6-difluoroisatin gave the title compound in 70% yield.

EXAMPLE 7

5-methoxyisatin

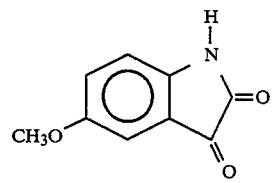

To a stirred solution of 12.6 g (75.6 mmol) of chloral hydrate in 168 mL water was added the following: 180 g (1.27 mole) sodium sulfate; 7.67 g (62.4 mmol) 4-methoxyaniline in 6 mL of concentrated HCl and 42 mL of water; and 15.4 g (224 mmol) of hydroxylamine hydrochloride in 70 mL of water. The mixture was heated slowly to 100° C. and kept at that temperature for 1 h. The mixture was cooled to room temperature, filtered and the precipitate washed with water and dried to give 81% yield of the anilide: $^1$H NMR (300 MHz, DMSO-d$_6$) δ 12.15 (s, 1H) 10.1 (s, 1H) 7.65 (s, 1H) 7.6 (d, 2H) 6.95 (d, 2H) 3.75 (s, 3H).

The crude anilide (10.8 g, 61 mmol) was added to 27 mL of concentrated sulfuric acid at 50° C., heated at 65° C. for 1 h, cooled to room temperature, and poured into 300 mL of ice. The solids were filtered and dried in vacuo over P$_2$O$_5$. The crude isatin was dissolved in boiling CH$_2$Cl$_2$ with 2% N-methylpyrrolidone and applied to a silica gel column. The product was eluted using a CH$_2$Cl$_2$:MeOH gradient 100% CH$_2$Cl$_2$ to (9:1) CH$_2$Cl$_2$:MeOH. 5-Methoxyisatin was obtained in 12% yield overall: mp 168°–172° C.; $^1$H NMR (300 MHz, DMSO-d$_6$) δ 10.85 (s, 1H) 7.17–7.24 (m, 1H) 7.1 (d, 1H) 6.87 (d, 1H) 3.75 (s, 3H); MS (M+CH$_4$CN)$^+$ 158.

EXAMPLE 8

5-Azaisatin

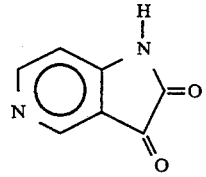

To a solution of 5-azaisatoic anhydride (1 mmol, Coppola, G. M. *Synthesis* 1980, 505) and allyl bromide (1.1 mmol) in DMF is added triethylamine (1.2 mmol) dropwise. The reaction mixture is allowed to stir at room temperature for 12 h after which time $CHCl_3$ is added and the organic layer is washed with water, dried ($MgSO_4$) and the solvent is evaporated to give N-allyl-5-azaisatoic anhydride.

A solution of N-allyl-5-azaisatoic anhydride (20 mmol) in DMF is added dropwise to a suspension of pulverized potassium cyanide (21 mmol) in DMF at 100° C. The reaction mixture is stirred at 100° C. for an additional 5 min after which time the mixture is poured into cold water and extracted with ether. The organic layer is dried ($Na_2SO_4$), filtered and the solvent is removed. Stirring the resulting residue in 2N hydrochloric acid overnight and adjusting the pH to 7 gives, upon filtration, N-allyl-5-azaisatin.

A solution of N-allyl-5-azaisatin (5.3 mmol), $(Ph_3P)_3RhCl$ (0.5 mmol) in aqueous toluene is stirred under a nitrogen atmosphere at room temperature overnight. The organic layer is dried ($MgSO_4$) and the solvent is evaporated. The residue is stirred in 1N HCl/MeOH for 15 min after which time the methanol is evaporated and the pH of the water is adjusted to 7. A precipitate is formed and purified by silica gel chromatography (1% MeOH:$CHCl_3$) to obtain the title compound.

EXAMPLE 9

6-Azaisatin

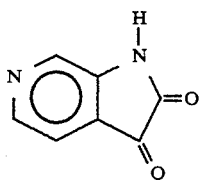

Using the procedure in Example 8 and substituting 4-azaisatoic anhydride (Coppola, G. M. *Synthesis* 1980, 505) for 5-azaisatoic anhydride gives the title compound.

EXAMPLE 10

7-Azaisatin

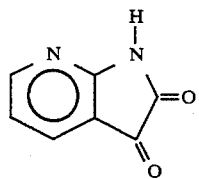

To a solution of 2-aminonicotinic acid (5 mmol) and sodium carbonate (5.1 mmol) in water is added triphosgene (1.6 mmol) at room temperature. The reaction mixture is allowed to stir for 16 h after which time the pH is adjusted to 3 and the resulting precipitate, 3-azaisatoic anhydride, is filtered.

Using the procedure in Example 8 and substituting 3-azaisatoic anhydride for 5-azaisatoic anhydride, gives the title compound.

EXAMPLE 11

4-Azaisatin

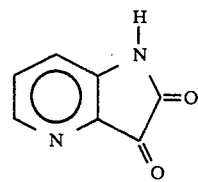

To a solution of 3-aminopicolinic acid (2 mmol, Hurd, C. D. et al. *J. Org. Chem.* 35:1471, 1970) and sodium carbonate (2.1 mmol) in water is added triphosgene (0.6 mmol). The reaction mixture is allowed to stir for 14 h at room temperature after which time the pH is adjusted to 3 and the resulting precipitate, 6-azaisatoic anhydride, is filtered.

Using the procedure in Example 8 and substituting 6-azaisatoic anhydride for 5-azaisatoic anhydride, gives the title compound.

EXAMPLE 12

2-Chloro-8-fluoroindolo[2,1-b]quinazoline-6,12-dione

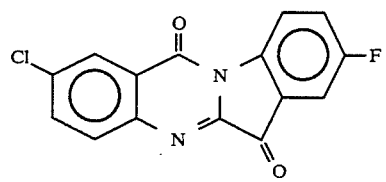

Isatoic anhydrides were prepared from 2-aminobenzoic acid derivatives using the following procedure. A solution of 2-amino-5-chlorobenzoic acid (1.56 g, 9.7 mmol) in 25 mL of dry THF and triphosgene (1.00 g, 3.3 mmol) was stirred at room temperature for 18 h. The resultant solid was filtered, washed with cold acetone, and dried under vacuum to give 1.56 g (89%) of 5-chloroisatoic anhydride.

To a suspension of NaH (10 mmol, 40 mg 60%) in 4 mL of DMF was added 10 mmol of 5-fluoroisatin in 2 mL of DMF. After 15 min, a solution of 5-chloroisatoic anhydride in 3 mL of DMF was added. The reaction mixture was stirred for 18 h, methanol (0.5 mL) and 20 mL of chloroform was added and the organic solution was washed with water, dried ($MgSO_4$) and concentrated to give a residue which was purified by silica gel chromatography ($CHCl_3$:$CH_3OH$). Yield 77%: mp 280°–282° C.

EXAMPLE 13

2-Chloro-8-nitroindolo[2,1-b]quinazoline-6,12-dione

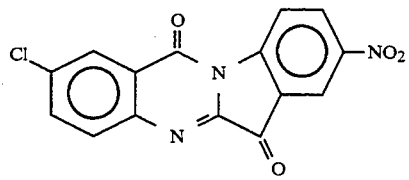

Using the procedure in Example 12 and substituting 8-nitroisatin for 5-fluoroisatin and recrystallization of the crude product from $CHCl_3$:ethyl acetate gave 44 mg of the title compound. Yield 1.3% yield: ¹H NMR (DMSO-d₆) δ 8.88–8.50 (brs, 3H), 8.40–8.24 (brs, 1H), 8.10–8.0 (brs, 2H).

EXAMPLE 14

2,3-Dimethoxyindolo[2,1-b]quinazoline-6,12-dione

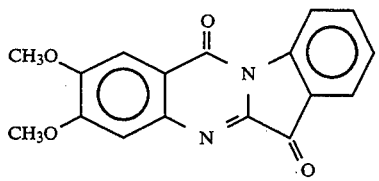

Using the procedure in Example 12, and substituting N-methylpyrrolidone (NMP) for N,N-dimethylformamide (DMF), 5,6-dimethoxyisatoic anhydride for 5-chloroisatoic anhydride and isatin for 5-fluoroisatin gave 367 mg (16%) of the title compound: mp 350° C. (dec); ¹H NMR(CDCl₃)δ 4.02–4.08 (d, 6H), 7.40–7.45 (m, 2H), 7.74–7.80 (m, 2H), 7.88–7.92 (m, 1H), 8.60–8.65 (d, 1H); MS (M+H)+ 308.

EXAMPLE 15

2-Chloroindolo[2,1-b]quinazoline-6,12-dione

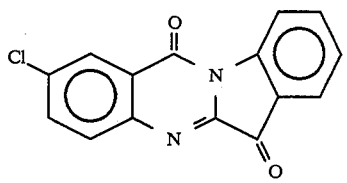

Using the procedure in Example 12, and substituting NMP for DMF and isatin for 5-fluoroisatin gave 53 mg (7%) of the title compound: mp 320° C. (dec); ¹H NMR(DMSO-d₆) δ 7.46–7.54 (m, 1H), 7.86–7.92 (m, 3H), 8.26–8.28 (m, 1H), 8.45–8.50 (m, 2H); MS (M+H)+ 282.

EXAMPLE 16

2-Nitroindolo[2,1-b]quinazoline-6,12-dione

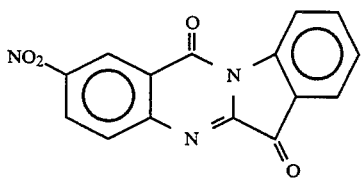

Using the procedure in Example 12, and substituting NMP for DMF, 5-nitroisatoic anhydride for 5-chloroisatoic anhydride and isatin for 5-fluoroisatin gave 495 mg (24%) of the title compound: mp 349° C. (dec); ¹H NMR(CDCl₃)δ 7.46–7.54 (m, 1H), 7.84–8.00 (m, 3H), 8.18–8.22 (m, 1H), 8.62–8.68 (m, 2H).

EXAMPLE 17

8-Bromoindolo[2,1-b]quinazoline-6,12-dione

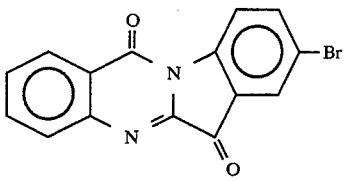

Using the procedure in Example 12 and substituting isatoic anhydride for 5-chloroisatoic anhydride and 5-bromoisatin for 5-fluoroisatin gave the title compound in 9% yield: mp 288°–290.2° C.; ¹H NMR (300 MHz, CDCl₃) δ 8.56 (d, 1H) 8.44 (d, 1H) 8.06 (s, 1H) 8.04 (s, 1H) 7.82–7.96 (m, 2H) 7.66–7.76 (m, 1H); MS (M+H)+ 328.

EXAMPLE 18

8-Nitroindolo[2,1-b]quinazoline-6,12-dione

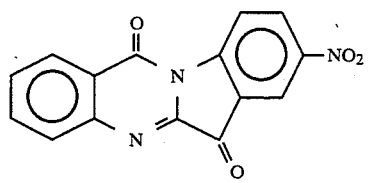

Using the procedure in Example 12 and substituting isatoic anhydride for 5-chloroisatoic anhydride and 5-nitroisatin for 5-fluoroisatin gave the title compound in 18% yield: mp 302.2°–303° C.; ¹H NMR (300 MHz, CDCl₃) δ 8.88 (d, 1H) 8.77 (d, 1H) 8.66–8.74 (m, 1H) 8.46–8.52 (m, 1H) 8.09 (d, 1H) 7.88–7.98 (m, 1H) 7.72–7.80 (m, 1H); MS (M+H)+ 293.

EXAMPLE 19

8-Fluoroindolo[2,1-b]quinazoline-6,12-dione

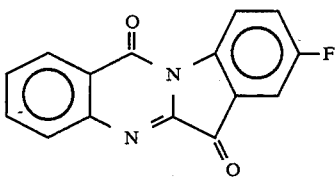

To a solution of potassium tert-butoxide (0.786 g, 7 mmol) in 10 mL of NMP was added 1.16 g (7 mmol) of 5-fluoroisatin in 50 mL of NMP. After 20 h at room temperature the reaction was quenched with 5 mL of methanol, 200 mL CHCl₃ and 100 mL water. The organic layer was separated, washed three times with water and dried (Na₂SO₄). Solvents were removed by reduced pressure and the resulting solid residue was purified by silica gel chromatography using CH₂Cl₂ as eluent. The title compound was obtained in a 34% yield: mp 273°–276° C.; ¹H NMR (300 MHz, DMSO-d₆) δ 8.48 (d, 1H) 8.33 (d, 1H) 7.90–8.02 (m, 3H) 7.71–7.82 (m, 1H); MS (M+CH₄CN)+ 308.

EXAMPLE 20

8-Chloroindolo[2,1-b]quinazoline-6,12-dione

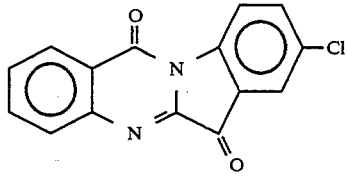

Using the procedure in Example 12 and substituting isatoic anhydride for 5-chloroisatoic anhydride and 5-chloroisatin for 5-fluoroisatin gave the title compound in 39% crude yield: mp 295°–296° C.; $^1$H NMR (300 MHz, DMSO-$d_6$) δ 8.46–8.53 (m, 1H), 8.33 (d, 1H), 7.96 (d, 2H), 7.69–7.84 (m, 3H); MS (M+H)$^+$ 283.

EXAMPLE 21

8-Methoxyindolo[2,1-b]quinazoline-6,12-dione

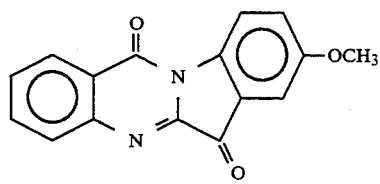

Using the procedure in Example 12 and substituting isatoic anhydride for 5-chloroisatoic anhydride and 5-methoxyisatin for 5-fluoroisatin gave the title compound in 24% yield: mp 267.6°–269° C.; $^1$H NMR (300 MHz, DMSO-$d_6$) δ 8.28 (d, 1H) 8.25 (d, 1H) 7.93 (d, 2H) 7.68–7.78 (m, 1H) 7.37–7.46 (m, 2H) 3.88 (s, 3H); MS (M+H)$^+$ 279.

EXAMPLE 22

8-Methylindolo[2,1-b]quinazoline-6,12-dione

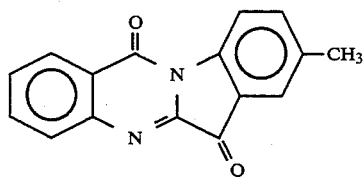

Using the procedure in Example 12 and substituting isatoic anhydride for 5-chloroisatoic anhydride and 5-methylisatin for 5-fluoroisatin gave the title compound in 36% yield: mp 282.8°–284.8° C.; $^1$H NMR (300 MHz, DMSO-$d_6$) δ 8.28–8.38 (m, 2H) 7.94 (d, 2H) 7.64–7.78 (m, 3H) 3.34 (s, 3H); MS (M+H)$^+$ 263.

EXAMPLE 23

8-Iodoindolo[2,1-b]quinazoline-6,12-dione

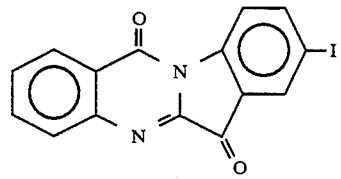

Using the procedure in Example 12 and substituting isatoic anhydride for 5-chloroisatoic anhydride and 5-iodoisatin for 5-fluoroisatin gave the title compound in 31% yield: mp 296.5°–297.3° C.; $^1$H NMR (300MHz, DMSO-$d_6$) δ 8.16–8.36 (m, 4H) 7.96 (2, H) 7.70–7.83 (m, 1H); MS (M+H)$^+$ 374.

EXAMPLE 24

2-Methylindolo[2,1-b]quinazoline-6,12-dione

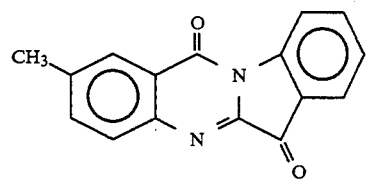

Using the procedure in Example 12 and substituting 5-methylisatoic anhydride for 5-chloroisatoic anhydride and isatin for 5-fluoroisatin gave the title compound in 34% yield: mp 266°–267° C.; $^1$H NMR (300 MHz, CDCl$_3$) δ 8.65 (d, 1H), 8.22 (s, 1H), 7.94 (d, 1H), 7.93 (d, 1H), 7.79 (dt, 1H), 7.66 ppm (1H), 7.45 (dt, 1H), 2.55 (s, 3H); MS (M+H)$^+$ 263, (M+CH$_4$CN)$^+$ 304.

EXAMPLE 25

1-Methylindolo[2,1-b]quinazoline-6,12-dione

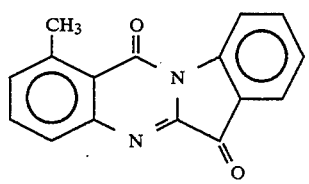

Using the procedure in Example 12 and substituting 6-methylisatoic anhydride for 5-chloroisatoic anhydride and isatin for 5-fluoroisatin gave the title compound in 31% yield: mp 304°–307° C.; $^1$H NMR (300 MHz, CDCl$_3$) δ 8.65 (d, 1H), 7.9 (t, 1H), 7.9 (t, 1H), 7.88 (t, 1H), 7.78 (t, 1H), 7.68 (t, 1H), 7.42 (dt, 1H), 7.41 (t, 1H), 3.0 (s, 3H); MS (M+H)$^+$ 263.1, (M+CH$_4$CN)$^+$ 304.

EXAMPLE 26

4-Methylindolo[2,1-b]quinazoline-6,12-dione

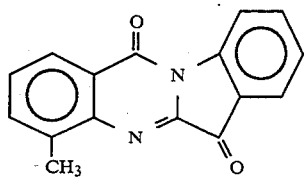

Using the procedure in Example 12 and substituting 3-methylisatoic anhydride for 5-chloroisatoic anhydride and isatin for 5-fluoroisatin gave the title compound in 31% yield: mp 247°–248° C.; $^1$H NMR (300 MHz, CDCl$_3$) δ 8.64 (d, 1H), 8.28 (d, 1H), 7.92 (d, 1H), 7.78 (dt, 1H), 7.70 (d, 1H), 7.55 (t, 1H), 7.43 (dt, 1H), 275 (s, 1H); MS (M+H)+ 263, (M+CH$_4$CN)+ 304.

EXAMPLE 27

2,8-Difluoroindolo[2,1-b]quinazoline-6,12-dione

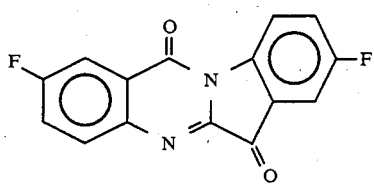

Using the procedure in Example 12, and substituting 5-fluoroisatoic anhydride for 5-chloroisatoic anhydride gave 161 mg (13%) of the title compound: mp 295.4°–296.2° C.; $^1$H NMR(DMSO-d$_6$) δ 7.51–7.80 (m, 3H), 8.03–8.10 (m, 2H), 8.46–8.52 (m, 1H). MS (M+H)+ 284.

EXAMPLE 28

2-Bromoindolo[2,1-b]quinazoline-6,12-dione

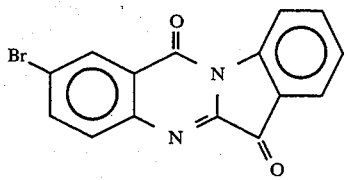

Using the procedure in Example 12, and substituting 5-bromoisatoic anhydride for 5-chloroisatoic anhydride and isatin for 5-fluoroisatin gave 635 mg (28%) of the title compound: mp 315°–316° C.; $^1$H NMR(CDCl$_3$) δ 7.56–7.62 (m, 1H), 7.94–8.02 (m, 3H), 8.18–8.24 (m, 1H), 8.48–8.58 (m, 2H); MS (M+H)+ 326.9.

EXAMPLE 29

2-Fluoroindolo[2,1-b]quinazoline-6,12-dione

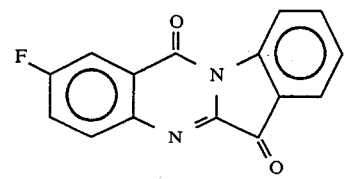

Using the procedure in Example 12, and substituting 5-fluoroisatoic anhydride for 5-chloroisatoic anhydride and isatin for 5-fluoroisatin gave 650 mg (57%) of the title compound: mp 295° C. (dec); $^1$H NMR (DMSO-d$_6$) δ 7.48–7.54 (m, 1H), 7.82–7.94 (m, 3H), 8.02–8.08 (m, 2H), 8.46–8.51 (m, 1H); MS (M+H)+ 267.1.

EXAMPLE 30

2-Amino-8-fluoroindolo[2,1-b]quinazoline-6,12-dione

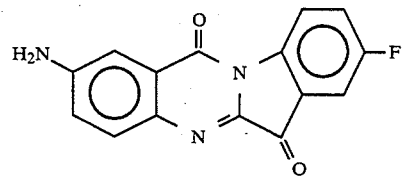

Using the procedure in Example 36 and substituting 5-aminoisatoic anhydride for 4-fluoroisatoic anhydride gave the title compound in 69% yield: mp >275° C. (dec); $^1$H NMR (300 MHz, DMSO-d$_6$) δ 8.5 (dd, 1H), 7.7 (m, 2H), 7.6 (d, 1H), 7.4 (d, 1H), 7.1 (dd, 1H), 6.44 (s, 2H).

EXAMPLE 31

9-Chloroindolo[2,1-b]quinazoline-6,12-dione

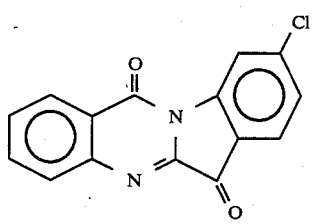

Using the procedure in Example 12 and substituting isatoic anhydride for 5-chloroisatoic anhydride and 6-chloroisatin for 5-fluoroisatin gave the title compound in 14% yield: mp 300.6°–303.1° C.; $^1$H NMR (300 MHz, DMSO-d$_6$) δ 8.49 (d, 1H) 8.35 (d, 1H) 7.89 (d, 2H) 7.94 (d, 1H) 7.72–7.82 (m, 1H) 7.55–7.62 (m, 1H); MS (M+CH$_4$CN)+ 324.

EXAMPLE 32

7-Chloroindolo[2,1-b]quinazoline-6,12-dione

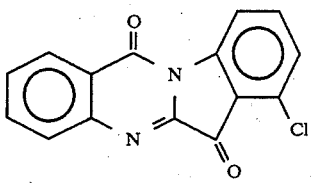

Using the procedure in Example 12 and substituting isatoic anhydride for 5-chloroisatoic anhydride and 4-chloroisatin for 5-fluoroisatin gave the title compound in 16% yield: mp 294°–295.7° C.; $^1$H NMR (300 MHz, DMSO-d$_6$) δ 8.49 (d, 1H) 8.33 (d, 1H) 7.97 (d, 2H) 7.81–7.90 (m, 1H) 7.72–7.80 (m, 1H) 7.52 (d, 1H); MS (M+H)+ 283.

EXAMPLE 33

8-Fluoro-4-methoxyindolo[2,1-b]quinazoline-6,12-dione

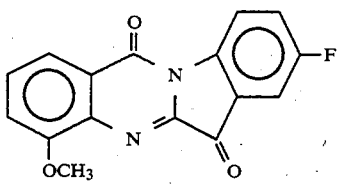

Using the procedure in Example 12 and substituting 3-methoxyisatoic anhydride for 5-chloroisatoic anhydride gave the title compound in 39% yield: mp >300° C. (dec); $^1$H NMR (300 MHz, DMSO-d$_6$) δ 8.7 (dd, 1H), 7.85 (dd, 1H), 7.8 (m, 1H), 7.75–7.66 (m, 2H), 7.56 (m, 1H), (d, 1H) 4.0 (s, 3H); MS (M+H)+ 297, (M+CH$_4$CN)+ 338.

EXAMPLE 34

2,4-Dimethy-8-fluoroindolo[2,1-b]quinazoline-6,12-dione

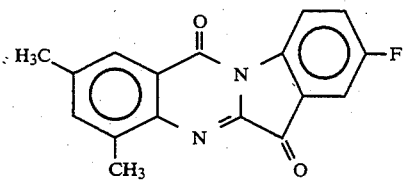

Using the procedure in Example 12 and substituting 3,5-dimethylisatoic anhydride for 5-chloroisatoic anhydride gave the title compound in 15% yield: mp 275°–277° C.; $^1$H NMR (300 MHz, CDCl$_3$) δ 8.65 (dd, 1H), 8.06 (s, 1H), 7.58 (dd, 1H), 7.52 (s, 1H), 7.46 (dd, 1H), 2.8 (s, 3H), 2.5 (s, 3H).

EXAMPLE 35

8-Fluoro-2-methylindolo[2,1-b]quinazoline-6,12-dione

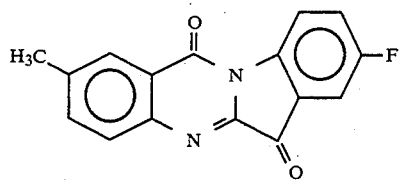

Using the procedure in Example 36 and substituting 5-methylisatoic anhydride for 4-fluoroisatoic anhydride gave the title compound in 43% yield: mp 300°–301° C.; $^1$H NMR (300 MHz, CDCl$_3$) δ 8.64 (dd, 1H), 8.22 (s, 1H), 7.90 (d, 1H), 7.66 (d, 1H), 7.57 (dd, 1H), 7.46 (dt, 1H), 2.55 (s, 3H).

EXAMPLE 36

3,8-Difluoroindolo[2,1-b]quinazoline-6,12-dione

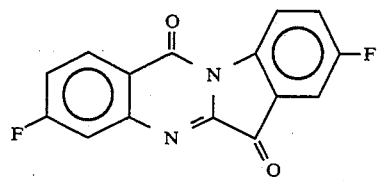

5-Fluoroisatin (2.20 g, 13.3 mmol) and 4-fluoroisatoic anhydride which was prepared according to the procedure in Example 12 (2.64 g, 14.6 mmol) were dissolved in 130 mL of dry dimethylformamide (DMF), DBU (2.22 g, 14.6 mmol) and 4-dimethylaminopyridine (DMAP, 0.16 g, 1.33 mmol) were added over 2 min. The reaction was stirred for 19 h and 130 mL of 0.2M HCl was added which produced a precipitate. The precipitate was filtered, washed with water (3×20 mL) and ethyl acetate (20 mL). The crude solid was purified by chromatography on silica gel eluting with chloroform giving the title compound in 20% yield: mp 297°–298° C.; $^1$H NMR (300 MHz, CDCl$_3$) δ 8.64 (dd, 1H), 8.45 (dd, 1H), 7.69 (dd, 1H), 7.58 (dd, 1H), 7.5 (dt, 1H), 7.4 (dt, 1H).

EXAMPLE 37

10-Fluoroindolo[2,1-b]quinazoline-6,12-dione

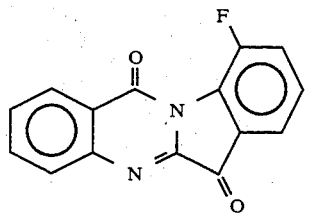

A solution of 7-fluoroisatin (300 mg, 1.8 mmol), isatoic anhydride (1.2 g, 7.3 mmol), and dimethylaminopyridine (222 mg, 2 mmol) in 5 mL of pyridine were heated at reflux temperature for 64 h. 50 mL of 0.2N HCl and 100 mL of chloroform were added and the chloroform layer was separated. The water layer was extracted with chloroform and the combined organic extracts were concentrated. Chromatography on silica gel eluting with chloroform gave the title compound in 14% yield: mp 264°–267° C.; ¹H NMR (300 MHz, CDCl₃) δ 8.46 (d, 1H) 8.02 (d, 1H) 7.82–7.92 (m, 1H) 7.79 (d, 1H) 7.64–7.74 (m, 1H) 7.52–7.64 (m, 1H) 7.40–7.49 (m, 1H).

EXAMPLE 38

1,8-Difluoroindolo[2,1-b]quinazoline-6,12-dione

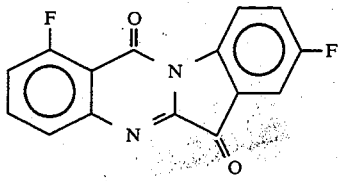

Using the procedure in Example 19 and substituting 6-fluoroisatoic anhydride for isatoic anhydride gave the title compound in 20% yield: mp 323°–325° C.; ¹H NMR (300 MHz, CDCl₃) δ 8.65 (dd, 1H), 7.89–7.82 (m, 2H), 7.58 (dd, 1H), 7.48 (dt, 1H), 7.35 (dt, 1H).

EXAMPLE 39

8-Fluoro-1-methylindolo[2,1-b]quinazoline-6,12-dione

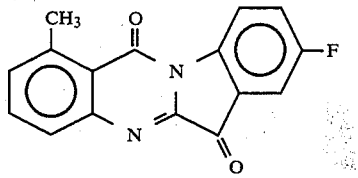

Using the procedure in Example 36 and substituting 6-methylisatoic anhydride for 4-fluoroisatoic anhydride gave the title compound in 35% yield: mp 300°–301° C.; ¹H NMR (300 MHz, CDCl₃) δ 8.63 (dd, 1H), 8.21 (s, 1H), 7.9 (d, 1H), 7.65 (d, 1H), 7.56 (dd, 1H), 7.46 (dt, 1H), 2.5 (s, 1H).

EXAMPLE 40

8-Fluoro-4-methylindolo[2,1-b]quinazoline-6,12-dione

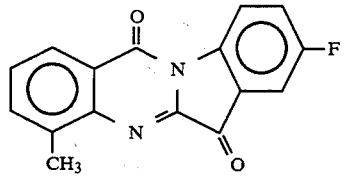

Using the procedure in Example 36 and substituting 3-methylisatoic anhydride for 4-fluoroisatoic anhydride gave the title compound in 42% yield: mp 255°–257° C.; ¹H NMR (300 MHz, CDCl₃) δ 8.61 (dd, 1H), 8.26 (d, 1H), 7.68 (d, 1H), 7.56 (dt, 1H), 7.52 (dt, 1H), 7.44 (dt, 1H), 2.75 (s, 3H).

EXAMPLE 41

8,10-Difluoroindolo[2,1-b]quinazoline-6,12-dione

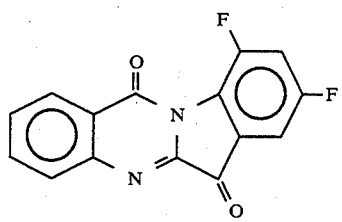

Using the procedure in Example 56 and substituting 2-aminobenzoic acid for 2-aminonicotinic acid and 5,7-difluoroisatin from Example 3 for isatin gave the title compound in 4.7% yield: mp 287°–290° C.; ¹H NMR (300 MHz, CDCl₃) δ 8.47 (d, 1H) 8.02 (d, 1H) 7.84–7.92 (m, 1H) 7.66–7.76 (m, 1H) 7.48–7.54 (m, 1H) 7.30–7.40 (m, 1H).

EXAMPLE 42

8-Carboethoxyindolo[2,1-b]quinazoline-6,12-dione

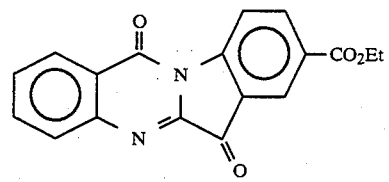

Using the procedure in Example 56 and substituting 2-aminobenzoic acid for 2-aminonicotinic acid and 5-carboethoxyisatin for 5-fluoroisatin gave the title compound in 30% yield: mp 270.5°–272.7° C.; ¹H NMR (300 MHz, CDCl₃) δ 8.71 (d, 1H) 8.59 (s, 1H) 8.42–8.54 (m, 2H) 8.05 (d, 1H) 7.84–7.94 (m, 1H) 7.66–7.76 (m, 1H) 4.38–4.5 (m, 2H) 1.4–1.5 (m, 3H).

EXAMPLE 43

4 8-Difluoroindolo[2,1-b]quinazoline-6,12-dione

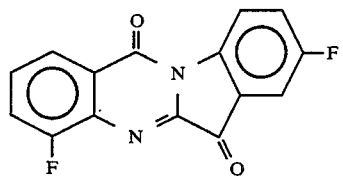

Using the procedure in Example 36 and substituting 3-fluoroisatoic anhydride for 4-fluoroisatoic anhydride gave the title compound in 16% yield: mp >300° C. (dec); ¹H NMR (300 MHz, DMSO-d₆) δ 8.51 (dd, 1H), 8.16 (d, 1H), 7.82–7.92 (m, 2H), 7.71–7.82 (m, 2H); MS (M+H)⁺ 285.

EXAMPLE 44

8,9-Difluoroindolo[2,1-b]quinazoline-6,12-dione

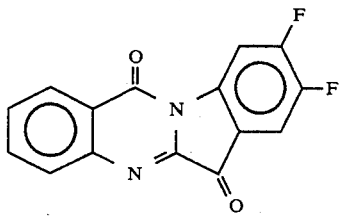

Using the procedure in Example 36 and substituting 5,6-difluoroisatin for 5-fluoroisatin and isatoic anhydride for 4-fluoroisatoic anhydride gave the title compound in 2% yield: mp >250° C. (dec); $^1$H NMR (300 MHz, DMSO-d$_6$) δ 8.54 (dd, 1H) 8.42 (d, 1H), 8.25 (d, 1H), 7.9 (dd, 1H), 7.78-7.68 (q, 2H); MS (M+H)+ 285.

EXAMPLE 45

8-Fluoro-1-(4-methylpiperazinyl)indolo[2,1-b]quinazoline-6,12-dione

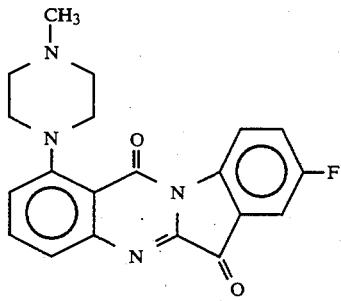

Using the procedure in Example 47 and substituting 1,8-difluoroindolo[2,1,b]quinazoline-6-12-dione for 9-chloroindolo[2,1-b]quinazoline-6,12-dione gave the title compound in 60% yield: mp 232°-233° C.; $^1$H NMR (300 MHz, CDCl$_3$) δ 8.72 (dd, 1H), 7.71 (t, 1H), 7.62 (d, 1H), 7.56 (dd, 1H), 7.46 (dt, 1H), 7.22 (d, 1H), 3.25 (s, 4H), 2.8 (s, 4H), 2.4 (s, 3H); MS (M+H)+ 365.

EXAMPLE 46

7-(4-Methylpiperazinyl)indolo[2,1-b]quinazoline-6,12-dione

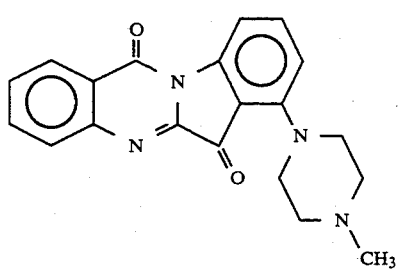

Using the procedure in Example 47 and substituting 7-chloroindolo[2,1-b]quinazoline-6-12-dione (0.3 mmol) for 9-chloroindolo[2,1-b]quinazoline-6,12-dione gave 85 mg of the title compound. Yield 85%; mp 207° C. (dec); $^1$H NMR(CDCl$_3$) δ 8.55 (brd, 1H), 8.10 (brd, 1H), 8.0 (brd, 1H), 7.83 (brt, 1H), 7.63 (brt, 1H), 7.56 (brt, 1H), 6.82 (brd, 1H), 3.5 (brs, 4H), 2.7 (brs, 4H).

EXAMPLE 47

9-(4-Methylpiperazinyl)indolo[2,1-b]quinazoline-6,12-dione

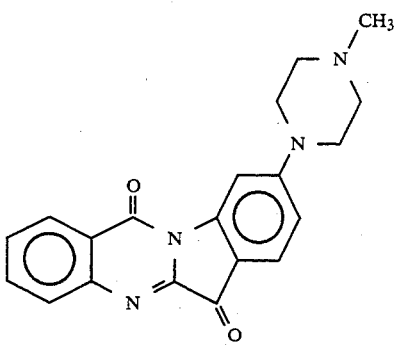

9-Chloroindolo[2,1-b]quinazoline-6,12-dione (Example 31, 155 mg, 0.55 mmol), N-methylpiperazine (75 μL, 0.68 mmol) and 3 mL of NMP were stirred at at 70° C. for 1 h. Chloroform (50 mL) was added and the mixture was washed with water (3×100 mL), dried (Na$_2$SO$_4$), filtered and solvent removed in vacuo to give the crude product. Silica gel chromatography purification of the residue using (95:5) chloroform:methanol as eluent gave 101 mg (53%) of the title compound: mp 214° C. (dec); $^1$H NMR(CDCl$_3$) δ 2.40 (s, 3H), 2.55-2.65 (m, 4H), 3.60-3.70 (m, 4H), 6.68-6.74 (dd, 1H), 760-7.70 (t, 1H), 7.73-7.80 (m, 1H), 7.80-7.86 (m, 1H), 7.99-8.05 (d, 1H), 8.10-8.14(d, 1H), 8.36-8.42 (d, 1H); MS (M+H)+ 347.2.

EXAMPLE 48

8-Fluoro-3-(4-methylpiperazinyl)indolo[2,1-b]quinazoline-6,12-dione

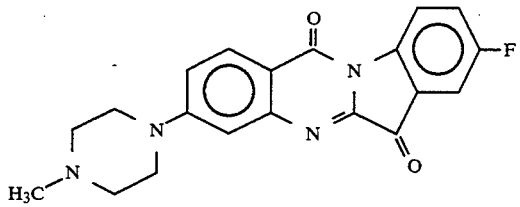

Using the procedure in Example 47 and substituting 3,8-difluoroindolo [2,1-b]quinazoline-6-12-dione for 9-chloroindolo[2,1-b]quinazoline-6,12-dione gave the title compound in 60% yield: mp 242°-244° C.; $^1$H NMR (300 MHz, CDCl$_3$) δ 8.61 (dd, 1H), 8.22 (d, 1H), 7.54 (dd, 1H), 7.45 (dt, 1H), 7.31 (d, 1H), 7.16 (dd, 1H), 3.50-3.41 (dt, 4H), 2.70-2.61 (dt, 4H), 2.35 (s, 3H); MS (M+H)+ 365.

EXAMPLE 49

8-Fluoro-9-(4-methylpiperazinyl)indolo[2,1-b]quinazoline-6,12-dione

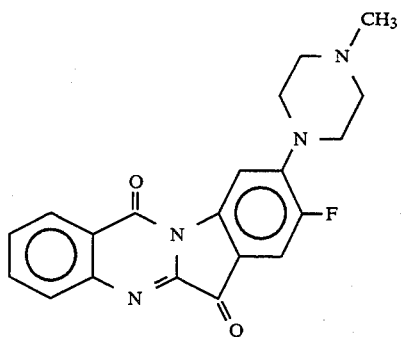

Using the procedure in Example 36 and substituting 5-fluoro-6-(4-methylpiperazinyl)isatin (from Example 4) for 5-fluoroisatin and isatoic anhydride for 4-fluoroisatoic anhydride gave the title compound in 24% yield: mp 257°–258° C.; $^1$H NMR (300 MHz, CDCl$_3$) δ 8.39 (d, 1H), 8.15 (d, 1H), 8.01 (d, 1H), 7.85 (t, 1H), 7.66 (t, 1H), 7.47 (d, 1H), 3.55-3.45 (dt, 4H), 2.70-2.62 (dt, 4H), 2.40 (s, 3H); MS (M+H)+ 365.

EXAMPLE 50

8,10-Difluoro-9-(4-Methylpiperazinyl)indolo[2,1-b]quinazoline-6,12-dione

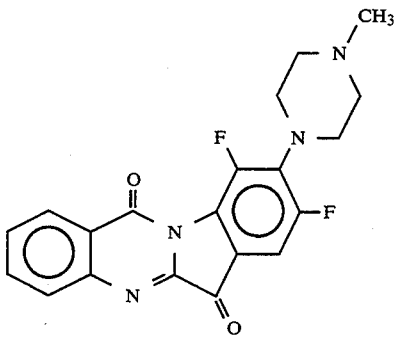

Using the procedure in Example 37 and substituting 5,7-difluoro-6-(4-methylpiperazinyl)isatin from Example 6 for 7-fluoroisatin gave the title compound in 3.4% yield: MS (M+H)+ 383.

EXAMPLE 51

3,8-Difluoro-9-(4-Methylpiperazinyl)indolo[2,1-b]quinazoline-6,12-dione

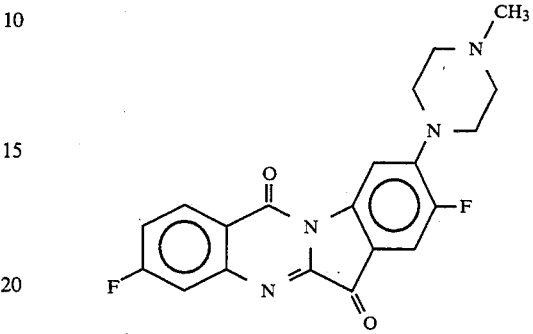

Using the procedure in Example 36 and substituting 5-fluoro-6-(4-methylpiperazinyl)isatin (from Example 4) for 5-fluoroisatin gave the title compound in 34% yield: mp>250° C. (dec); $^1$H NMR (300 MHz, CDCl$_3$) δ 8.40 (dd, 1H), 8.13 (d, 1H), 7.66 (dd, 1H), 7.48 (dd, 1H), 7.35 (dt, 1H), 3.55-3.46 (dt, 4H), 2.65-2.56 (dt, 4H), 2.40 (s, 3H).

EXAMPLE 52

9-(4-t-Butyloxycarbonylpiperazinyl)indolo[2,1-b]quinazoline-6,12-dione

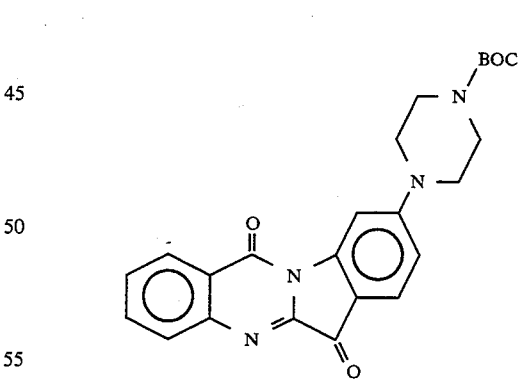

Using the procedure in Example 47, and substituting t-butyl 1-piperazinecarboxylate for N-methylpiperazine gave 80 mg (99%) of the title compound: mp 226°–228° C.; $^1$H NMR(CDCl$_3$) δ 1.5-1.6 (d, 9H), 3.65 (s, 8H), 6.67-6.72 (dd, 1H), 7.62-7.64 (dt, 1H), 7.66-7.81(d, 1H), 7.81-7.88(dt, 1H), 8.00-8.03 (d, 1H), 8.09-8.12 (d, 1H), 8.38-8.42 (dd, 1H).

EXAMPLE 53

8-Fluoro-9-(3-methyl-4-t-butyloxycarbonylpiperazinyl-)indolo [2,1-b]quinazoline-6,12-dione

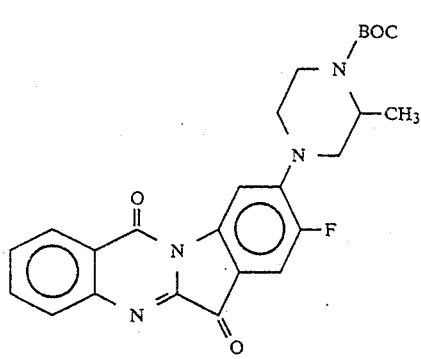

Using the procedure in Example 36 and substituting 5-fluoro-6-(3-methyl-4-t-butyloxycarbonylpiperazinyl-)isatin (from Example 5) for 5-fluoroisatin and isatoic anhydride for 4-fluoroisatoic anhydride gave the title compound in 31% yield: mp 234°–237° C.; $^1$H NMR (300 MHz, CDCl$_3$) δ 8.40 (d, 1H), 8.15 (d, 1H), 8.00 (d, 1H), 7.85 (t, 1H), 7.65 (t, 1H), 7.50 (d, 1H), 4.4 (br s, 1H), 4.00 (d, 1H), 3.75 (dd, 2H), 3.35 (dt, 2H), 3.15 (t, 1H), 1.5 (s, 9H).

EXAMPLE 54

8-Fluoro-9-(3-methylpiperazinyl)indolo[2,1-b]quinazoline-6,12-dione

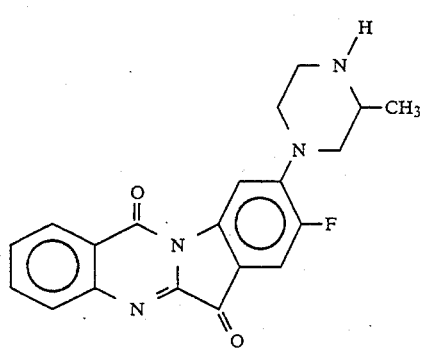

A solution of 8-fluoro-9-(3-methyl-4-t-butyloxycarbonylpiperazinyl)-indolo[2,1-b]quinazoline-6-12-dione (0.19 g, 0.4 mmol) (from Example 53) in methylene chloride (7 mL) and trifluoroacetic acid (7 mL) was stirred for 1 h. Chloroform was added and the chloroform/methylene chloride solution was washed with saturated sodium bicarbonate. The organic layer was separated, dried and concentrated to give a solid. Purification of the crude product by silica gel chromatography (chloroform eluent) gave the title compound in 75% yield: mp 225°–227° C.; $^1$H NMR (300 MHz, CDCl$_3$) δ 8.40 (d, 1H), 8.18 (d, 1H), 8.03 (d, 1H), 7.85 (t, 1H), 7.65 (t, 1H) 7.50 (d, 1H), 4.3 (m, 1H), 3.86-3.76 (m, 2H), 3.13-3.04 (m, 4H), 2.8 (t, 1H) 1.75 (s, 3H).

EXAMPLE 55

Thiophene Analog

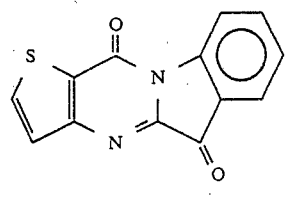

Methyl 3-amino-2-thiophenecarboxylate (1.88 g, 11.9 mmol) and 2-chloro-3H-indole-3-one (0.56 g, 3.98 mmol, prepared according to the procedure of Grimshaw, J. et al, *Synthesis* 1974, 496) were dissolved in 20 mL of glacial acetic acid and the mixture was heated at reflux temperature for 45 min. The reaction mixture was cooled to room temperature and quenched with 50 mL of water. The aqueous layer was extracted with 4×100 mL of chloroform. The organic extracts were washed with 50 mL of 6N HCl, dried (Na$_2$SO$_4$), filtered and solvent removed in vacuo to give 1.57 g of crude product. Purification of the residue by silica gel chromatography using chloroform as eluent gave 0.48 g (47%) of the title compound: mp 279° C. (dec); $^1$H NMR(CDCl$_3$) δ 7.40–7.70 (m, 1H), 7.58–7.60 (d, 1H), 7.75–7.82 (m, 1H), 7.88–7.92 (d, 2H), 8.60–8.64 (d, 1H).

EXAMPLE 56

Indolo[2,1-b]4-azaquinazoline-6,12-dione

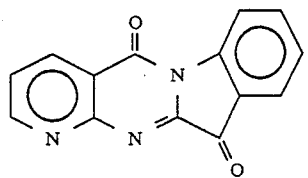

To a solution of 2-[1H-benzotriazole-1-yl]-1,1,3,3-tetramethyluronium hexafluorophosphate (HBTU, 2.85 g, 7.52 mmol), N-methylmorpholine (NMM, 1.5 mL, 13.7 mmol), and 2-aminonicotinic acid (1.04 g, 7.53 mmol) in 50 mL of dry DMF was added a solution of isatin (1.01 g, 6.83 mmol) and DBU (1,8-diazabicyclo[5.4.0]undec-7-ene, 2.5 mL, 16.7 mmol) in 40 mL dry DMF over 12 min at room temperature. After 20 h, the reaction mixture was quenched with 200 mL of 1N citric acid solution. Water was added to make the final volume 1 L. The mixture was filtered to give 520 mg of residue. The filtrate was extracted with 5×100 mL of chloroform, washed with 2×300 mL of water. The organic layer was dried over anhydrous sodium sulfate, filtered and solvent removed in vacuo to give an oil. Silica gel chromatography purification of the oil and residue using (5:1) methylene chloride:ethyl acetate as eluent gave the title compound in 40% yield: mp 272° C. (dec); $^1$H NMR (DMSO-d$_6$) δ 7.48–7.56 (m, 1H), 7.72–7.78 (m, 1H), 7.86–7.96 (m, 2H), 8.43–8.48 (m, 1H), 8.68–8.74 (m, 1H), 9.05–9.10 (m, 1H). MS (M+H)$^+$ 250.

EXAMPLE 57

8-Fluoroindolo[2,1-b]4-azaquinazoline-6,12-dione

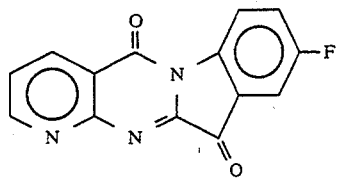

Using the procedure in Example 56, and substituting 5-fluoroisatin for isatin gave 0.78 g (44%) of the title compound: mp 308° C. (dec); $^1$H NMR (DMSO-d$_6$) δ 7.72–7.81 (m, 2H), 7.84–7.88 (q, 1H), 8.45–8.52 (m, 1H), 8.71–8.76 (dd, 1H), 9.08–9.12 (m, 1H).

EXAMPLE 58

8-Fluoroindolo[2,1-b]pteridine-6,12-dione

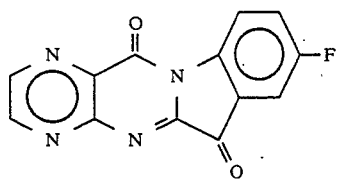

Using the procedure in Example 56, and substituting 3-aminopyrazine-2-carboxylic acid for 2-aminonicotinic acid and 5-fluoroisatin for isatin gave 79 mg (6%) of the title compound: mp 336° C. (dec); $^1$H NMR(DMSO-d$_6$) δ 7.65–8.00 (m, 2H), 8.50 (s, 1H), 9.05–9.20 (m, 2H); MS (M+H)+ 269.

EXAMPLE 59

8-Chloroindolo[2,1-b]4-azaquinazoline-6,12-dione

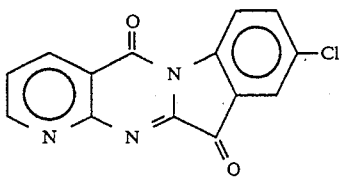

Using the procedure in Example 56, and substituting 5-chloroisatin for isatin gave the title compound: mp 312° C.

EXAMPLE 60

Indolo[2,1-b]pteridine-6,12-dione

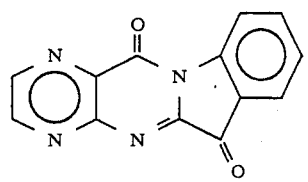

Using the procedure in Example 56 and substituting 3-aminopyrazine-2-carboxylic acid for 2-aminonicotinic acid gives the title compound.

EXAMPLE 61

7-Chloroindolo[2,1-b]4-azaquinazoline-6,12-dione

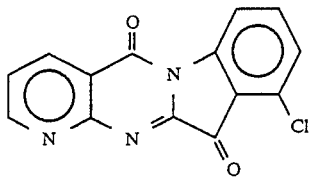

Using the procedure in Example 56 and substituting 4-chloroisatin for isatin gives the title compound.

EXAMPLE 62

9-Chloroindolo[2,1-b]4-azaquinazoline-6,12-dione

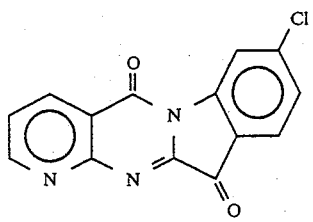

Using the procedure in Example 56 and substituting 6-chloroisatin for isatin gives the title compound.

EXAMPLE 63

8-Bromoindolo[2,1-b]4-azaquinazoline-6,12-dione

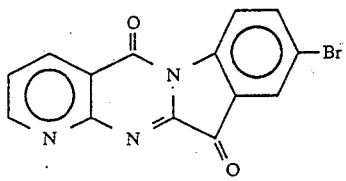

Using the procedure in Example 56 and substituting 5-bromoisatin for isatin gave the title compound in 34% yield: mp decomposes 322°–325° C.; $^1$H NMR (300 MHz, DMSO-d$_6$) δ 9.06–9.12 (m, 1H) 8.68–8.76 (m, 1H) 8.39 (d, 1H) 8.04–8.16 (m, 2H) 7.72–7.82 (m, 1H).

EXAMPLE 64

8-Carboethoxyindolo[2,1-b]4-azaquinazoline-6,12-dione

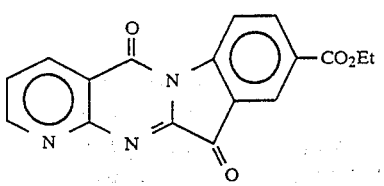

Using the procedure in Example 56 and substituting 8-carboethoxyisatin for isatin gives the title compound.

EXAMPLE 65

8,9-Difluoroindolo[2,1-b]4-azaquinazoline-6,12-dione

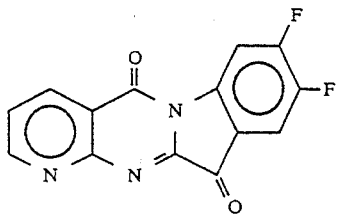

Using the procedure in Example 56 and substituting 5,6-difluoroisatin (prepared in Example 1) for isatin, gives the title compound.

EXAMPLE 66

8-Nitroindolo[2,1-b]4-azaquinazoline-6,12-dione

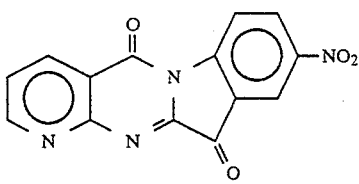

Using the procedure in Example 56 and substituting 5-nitroisatin for isatin, gives the title compound.

EXAMPLE 67

3,8-Difluoroindolo[2,1-b]4-azaquinazoline-6,12-dione

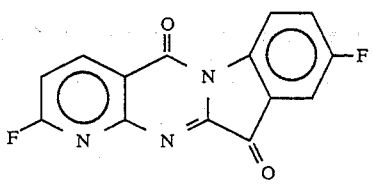

Using the procedure in Example 56 and substituting 5-fluoroisatin for isatin and 2-amino-6-fluoropyridine-3-carboxylic acid (Rogers et al. U.S. Pat. No. 4,383,851, 1983) for 2-aminonicotinic acid gives the title compound.

EXAMPLE 68

8-Fluoro-3-(4-methylpiperazinyl)indolo[2,1-b]4-azaquinazoline-6,12-dione

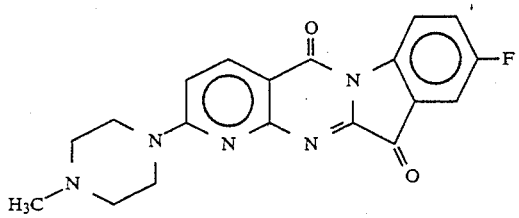

Using the procedure in Example 47 and substituting 3,8-difluoroindolo[2,1-b]-4-azaquinazoline-6,12-dione (Example 67) for 9-chloroindolo[2,1-b]quinazoline-6,12-dione gives the title compound.

EXAMPLE 69

2,3-Dichloro-8-fluoroindolo[2,1-b]pteridine-6,12-dione

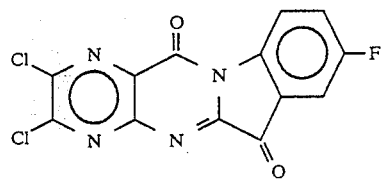

Using the procedure in Example 55 and substituting methyl 3-amino-5,6-dichloro-2-pyrazinecarboxylate for methyl 3-amino-2-thiophenecarboxylate and 5-fluoro-2-chloro-3H-indole-3-one (prepared from 5-fluoroisatin according to Grimshaw, J. et al, *Synthesis* 496, 1974) for 2-chloro-3H-indole-3-one gives the title compound.

EXAMPLE 70

2-Chloro-8-fluoro-3-(4-methylpiperazinyl)indolo[2,1-b]pteridine-6,12-dione

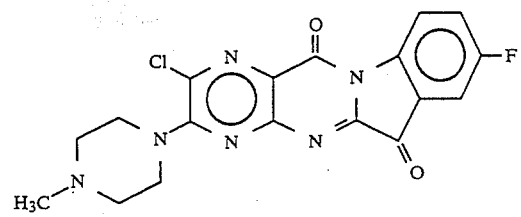

Using the procedure in Example 47, and substituting 2,3-dichloro-8-fluoroindolo[2,1-b]pteridine-6,12-dione (Example 69) for 9-chloroindolo[2,1-b]quinazoline gives the title compound.

EXAMPLE 71

2-Chloro-8-fluoroindolo[2,1-b]4-azaquinazoline-6,12-dione

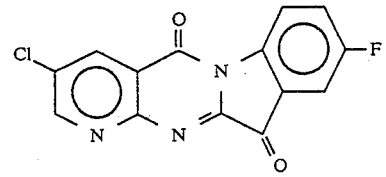

Using the procedure in Example 56 and substituting 5-fluoroisatin for isatin and 2-amino-5-chloronicotinic acid (Abu El-Haj et al., U.S. Pat. No. 3,917,624, 1975) for 2-aminonicotinic acid gives the title compound.

EXAMPLE 72

8-Fluoroindolo[2,1-b]1-azaquinazoline-6,12-dione

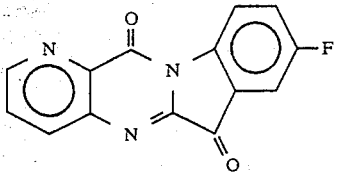

Using the procedure in Example 56 and substituting 5-fluoroisatin for isatin and 3-aminopicolinic acid (Hurd, C. D. et al., *J. Org. Chem.*, 35:1471, 1970) for 2-aminonicotinic acid gives the title compound.

EXAMPLE 73

8-Fluoroindolo[2,1-b]2-azaquinazoline-6,12-dione

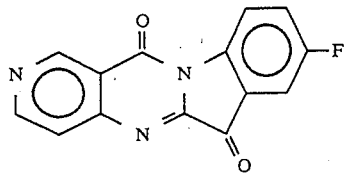

Using the procedure in Example 56 and substituting 5-fluoroisatin for isatin and 4-aminonicotinic acid (Turner, J. A., *J. Org. Chem.* 55:4744, 1990) for 2-aminonicotinic acid gives the title compound.

EXAMPLE 74

8-Fluoroindolo[2,1-b]3-azaquinazoline-6,12-dione

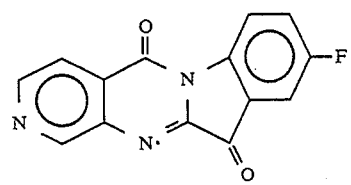

Using the procedure in Example 56 and substituting 5-fluoroisatin for isatin and 3-aminoisonicotinic acid (Turner, J. A., *J. Org. Chem.* 48:3401, 1983) for 2-aminonicotinic acid gives the title compound.

EXAMPLE 75

2-Fluoro-7-azaindolo[2,1-b]quinazoline-6,12-dione

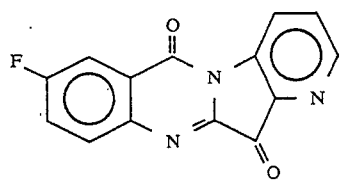

Using the procedure in Example 36 and substituting 4-azaisatin (Example 11) for 5-fluoroisatin and 5-fluoroisatoic anhydride for 4-fluoroisatoic anhydride gives the title compound.

EXAMPLE 76

2-Fluoro-8-azaindolo[2,1-b]quinazoline-6,12-dione

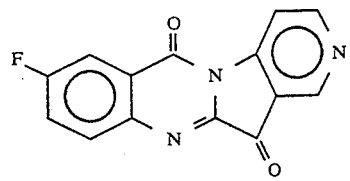

Using the procedure in Example 36 and substituting 5-azaisatin (Example 8) for 5-fluoroisatin and 5-fluoroisatoic anhydride for 4-fluoroisatoic anhydride gives the title compound.

EXAMPLE 77

2-Fluoro-9-azaindolo[2,1-b]quinazoline-6,12-dione

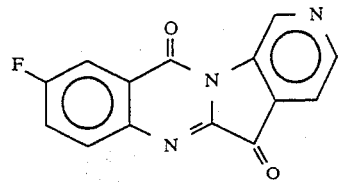

Using the procedure in Example 36 and substituting 6-azaisatin (Example 9, J. Parrick et al., *Tetrahedron Lett.* 25:3099, 1984) for 5-fluoroisatin and 5-fluoroisatoic anhydride for 4-fluoroisatoic anhydride gives the title compound.

EXAMPLE 78

2-Fluoro-10-azaindolo[2,1-b]quinazoline-6,12-dione

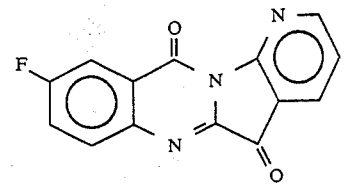

Using the procedure in Example 36 and substituting 7-azaisatin (Example 10, J. Parrick et al., *J. Chem. Soc. Perkin I* 2009, 1989) for 5-fluoroisatin and 5-fluoroisatoic anhydride for 4-fluoroisatoic anhydride gives the title compound.

EXAMPLE 79

8-(2-Glucosylaminocarbonyl)indolo[2,1-b]quinazoline-6,12-dione

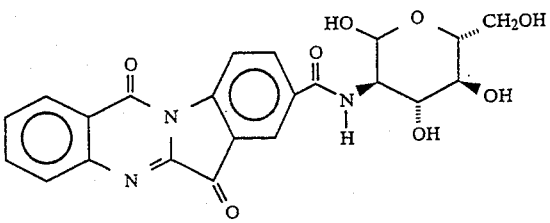

A solution of 8-carboethoxyindolo[2,1-b]quinazoline-6,12-dione (2 mmol, from Example 42) in 3 mL of trimethylsilyl iodide (TMSI) is heated to 100° C. for 4 h. The reaction mixture is cooled to room temperature, diluted with ether, and 3 mL of 0.5N NaOH solution is added. The reaction mixture is acidified with 6N HCl and extracted with chloroform. The chloroform extracts are dried, filtered, and concentrated to give 8-carboxyindolo[2,1-b]quinazoline-6,12-dione.

To a solution of 8-carboxyindolo[2,1-b]quinazoline-6,12-dione (1 mmol) in 2 mL of DMF is added carbonyldiimidazole (CDI, 1 mmol). The reaction mixture is stirred at room temperature for 1 h and a solution of D-glucosamine (1 mmol) and dimethylaminopyridine (DMAP, 0.1 mmol) in 1 mL of DMF is added. The reaction mixture is stirred for an additional 72 h at room temperature and 5 mL of 1N HCl is added. The solution is extracted with chloroform and the chloroform extracts are washed with saturated NaHCO₃, dried (Na₂SO₄), concentrated, and purified by silica gel chromatography to give the title compound.

EXAMPLE 80

8-Pyrrolidine amide of
8-carboxyindolo[2,1-b]quinazoline-6,12-dione

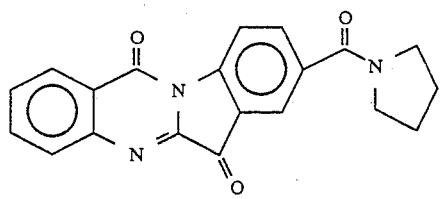

Using the procedure in Example 79 and substituting pyrrolidine for D-glucosamine gives the title compound.

EXAMPLE 81

2-(N-Ethoxycarbonyl)amino-8-fluoroindolo[2,1-b]quinazoline-6,12-dione

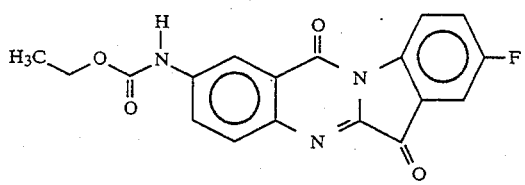

To a solution of 2-amino-8-fluoroindolo[2,1-b]quinazoline-6,12-dione (0.1 mmol) and sodium bicarbonate (0.2 mmol) in DMF (1 mM) is added ethyl chloroformate (excess) and N,N-dimethylaminopyridine (excess). The reaction mixture is allowed to stir for 24 h after which time chloroform is added and the organic layer is washed with 0.5N HCl, saturated sodium bicarbonate solution and brine. The organic layer is dried (MgSO₄), filtered and the solvent is evaporated. Silica gel chromatography (1% MeOH/CHCl₃) gives the title compound.

EXAMPLE 82

2-Octyl Indolo[2,1-b]4-azaquinazoline-6,12-dione
8-Carboxylate

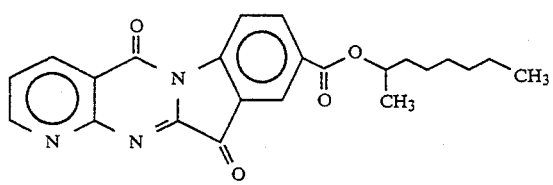

8-Carboethoxyindolo[2,1-b]-4-azaquinazoline-6,12-dione (10 mmol, from Example 4), titanium tetraisopropoxide (10 mmol) and 25 mL of 2-octanol are heated at 100° C. while ethanol and isopropanol are distilled. After 6 h, the reaction is cooled, excess 2-octanol is removed under high vac and the product is purified by silica gel chromatography using ethyl acetate:hexane.

EXAMPLE 83

3-Oxazolidinone Derivative of
8-Fluoroindolo[2,1-b]quinazoline-6,12-dione

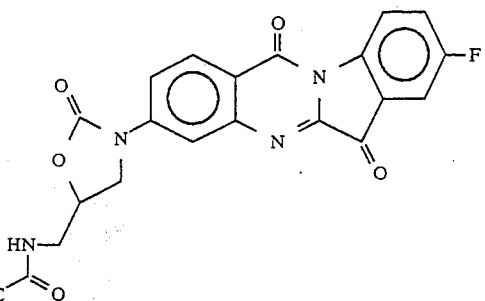

A solution of 3,8-difluoroindolo[2,1-b]quinazoline-6,12-dione (0.1 mmol, Example 36), t-butyl carbamate (0.11 mmol) and lithium hydride (0.12 mmol) in DMF (0.1 mM) is stirred at 70° C. for 12 h. The resulting reaction mixture is diluted with chloroform, washed with 0.1N HCl, sodium bicarbonate solution, dried (MgSO₄) and the solvent is evaporated. Silica gel chromatography (1% MeOH/CHCl₃) gives 3-(N-t-butyloxycarbonylamino)-8-fluoroindolo[2,1-b]quinazoline-6,12-dione.

A solution of 3-(N-t-butyloxycarbonylamino)-8-fluoroindolo[2,1-b]quinazoline-6,12-dione (0.5 mmol), (R)-glycidyl butyrate (0.55 mmol) and lithium hydride (0.60 mmol) in DMF is allowed to stir at room temperature overnight. The reaction mixture is diluted with CHCl₃, washed with 0.1N HCl, sodium bicarbonate solution, dried (MgSO₄) and the solvent is evaporated. Silica gel chromatography (1% MeOH/CHCl₃) gives 3-(5-hydroxymethyloxazolidin-3-yl)-8-fluoroindolo[2,1-b]quinazoline-6,12-dione.

A solution of 3-(5-hydroxymethyloxazolidin-3-yl)-8-fluoroindolo[2,1-b]-quinazoline-6,12-dione (0.1 mmol), tosyl chloride (0.12 mmol) and triethylamine (0.2 mmol) in dry DMF is allowed to stir at room temperature overnight. The reaction mixture is diluted with CHCl₃, washed with 0.1N HCl, sodium bicarbonate solution, dried (MgSO₄) and the solvent is evaporated to give 3-(5-tosyloxymethyloxazolidin-3-yl)-8-fluoroindolo[2,1-b]quinazoline-6,12-dione.

To a solution of 3-(5-tosyloxymethyloxazolidin-3-yl)-8-fluoroindolo[2,1-b]-quinazoline-6,12-dione (0.2 mmol) in DMF is added sodium azide (0.21 mmol). The reaction mixture is allowed to stir for 18 h at room temperature after which time CHCl₃ is added and the organic layer is washed with water, dried (MgSO₄) and the solvent is evaporated. Silica gel chromatography (1% MeOH/CHCl₃) gives 3-(5-azidomethyloxazolidin-3-yl)-8-fluoroindolo[2,1-b]quinazoline-6,12-dione.

A solution of 3-(5-azidomethyloxazolidin-3-yl)-8-fluoroindolo[2,1-b]-quinazoline-6,12-dione (0.05 mmol) and Pd/C (10%) in acetic anhydride (0.1 mM) is allowed to stir at room temperature under a hydrogen atmosphere for 12 h. The volatiles are evaporated, CHCl₃ is added and the organic layer is washed with 0.1N HCl, sodium bicarbonate and brine. The solvent is then evaporated and silica gel chromatography (1% MeOH/CHCl₃) gives the title compound.

EXAMPLE 84

2-Oxazolidinone Derivative of 8-fluoroindolo[2,1-b]quinazoline-6,12-dione

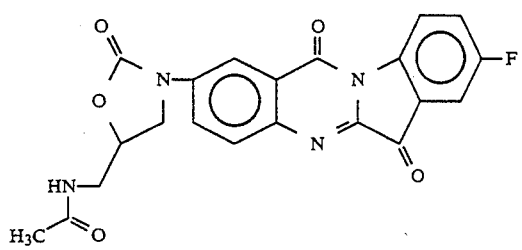

Using the procedure in Example 83 and substituting 2-(N-t-butyl-oxycarbonylamino)-8-fluoroindolo[2,1-b]quinazoline-6,12-dione for 2-(N-ethoxy-carbonylamino)-8-fluoroindolo[2,1-b]quinazoline-6,12-dione (Example 81) gives the title compound.

EXAMPLE 85

3-(R)-Cycloserinyl-8-fluoroindolo[2,1-b]quinazoline-6,12-dione

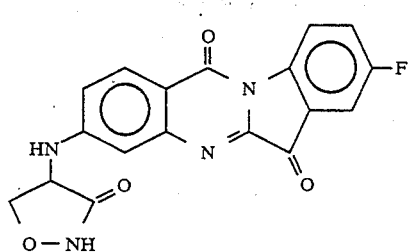

Using the procedure in Example 47 and substituting (R)-cycloserine for N-methylpiperazine gives the title compound.

EXAMPLE 86

Benzoic Amide of 2-amino-8-fluoroindolo[2,1-b]quinazoline-6,12-dione

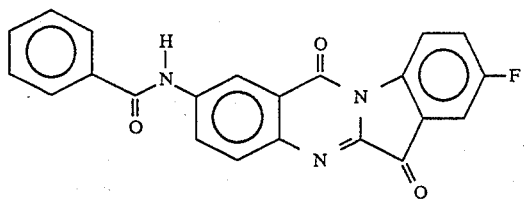

Using the procedure in Example 81 and substituting benzoyl chloride for ethyl chloroformate gives the title compound.

EXAMPLE 87

2-Quinolinecarboxamide of 2-Amino-8-fluoro-indolo[2,1-b]quinazoline-6,12-dione

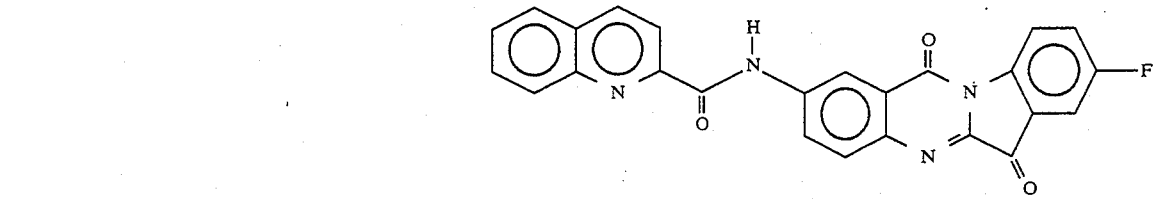

Using the procedure in Example 81 and substituting quinoxaloyl chloride for ethyl chloroformate gives the title compound.

EXAMPLE 88

Dodecacarboxamide of 8-Fluoroindolo[2,1-b]quinazoline-6,12-dione

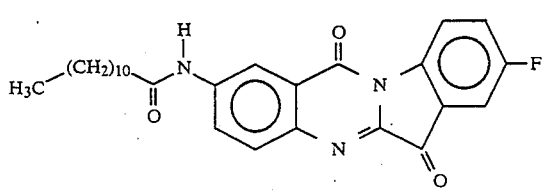

Using the procedure in Example 81 and substituting lauroyl chloride for ethyl chloroformate gives the title compound.

EXAMPLE 89

9-piperazinylindolo[2,1-b]quinazoline-6,12-dione

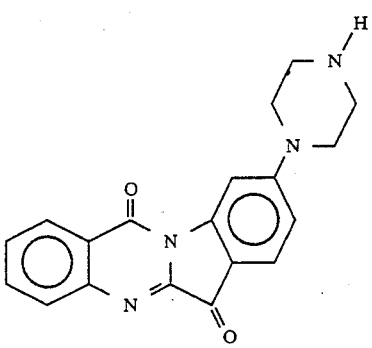

To a solution of 9-(4-t-butyloxycarbonylpiperazinyl-)indolo[2,1-b]quinazoline-6,12-dione (Example 52, 40 mg, 925 μmol) in 1 mL of methylene chloride was added 1 mL of trifluoroacetic acid (TFA). After 30 min, saturated sodium bicarbonate was added. The aqueous layer was separated and extracted with 3×50 mL of chloroform, dried over anhydrous sodium sulfate, filtered and solvent removed in vacuo to give 37 mg of crude product. Silica gel chromatorgraphy using (95:5) methylene chloride:methanol as eluent gave 24 mg (77%) of the title compound: mp 214° C. (dec); $^1$H NMR(DMSO-d$_6$) δ 2.5 (s, 4H), 3.5 (s, 4H), 6.88–6.94 (dd, 1H), 7.62–7.66 (d, 1H), 7.68–7.75 (m, 1H), 7.90–7.94 (m, 2H), 7.95–7.98 (m, 1H), 8.26–8.31 (d, 1H).

EXAMPLE 90

Orotic Acid analog

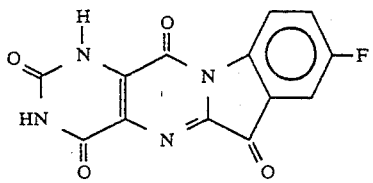

Using the procedure in Example 56, and substituting 5-aminoorotic acid for 2-aminonicotinic acid and 5-fluoroisatin for isatin gave 1.1 g (73%) of the title compound: mp >400° C.; $^1$H NMR(DMSO-d$_6$) δ 7.70–7.87 (m, 2H), 8.38–8.45 (m, 1H), 11.9 (s, 2H); MS (M+H)+ 301.

EXAMPLE 91

Pyrazole analog

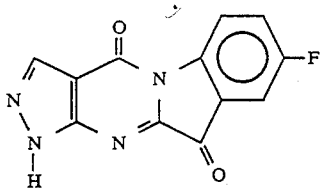

Using the procedure in Example 56, and substituting 5-fluoroisatin for isatin and 3-amino-4-pyrazolecarboxylic acid for 2-aminonicotinic acid gives the title compound.

EXAMPLE 92

1-Phenyl-pyrazole analog

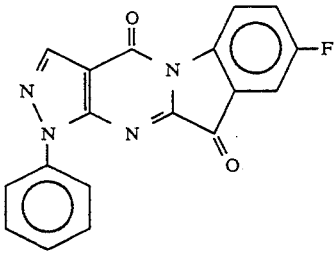

Using the procedure in Example 69 and substituting ethyl 5-amino-1-phenyl-4-pyrazolecarboxylate for 3-amino-5,6-dichloro-2-pyrazinecarboxylate, gives the title compound.

EXAMPLE 93

3-Benzylimidazole analog

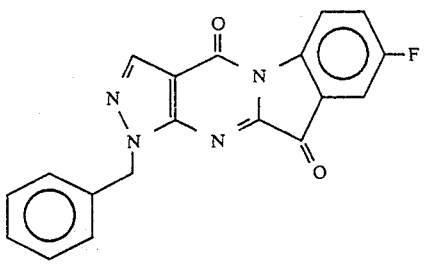

Using the procedure in Example 69 and substituting ethyl 5-amino-1-benzylimidazole-4-carboxylate (Mackenzie, G. et al, *J. Chem. Soc., Perkin Trans. I* 2544, 1988) for methyl 3-amino-5,6-dichloro-2-pyrazinecarboxylate gives the title compound.

EXAMPLE 94

Thiazole analog

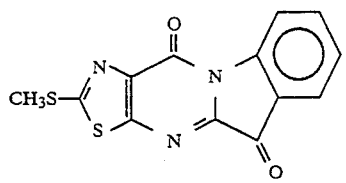

Using the procedure in Example55 and substituting ethyl 5-amino-2-(methylthio)thiazol-4-carboxylate (Wamhoff, H. et al, *Synthesis* 107, 1993) for methyl 3-amino-2-thiophenecarboxylate gives the title compound.

EXAMPLE 95

Thiazole analog

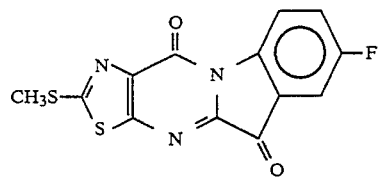

Using the procedure in Example 69 and substituting ethyl 4-amino-2-(methylthio)thiazol-5-carboxylate (Wamhoff, H et al, *Synthesis* 107, 1993) for methyl 3-amino-5,6-dichloro-2-pyrazinecarboxylate gives the title compound.

EXAMPLE 96

In Vitro Inhibition of Mycobacteria

The Proportion Method protocols described by the National Committee for Clinical Laboratory Standards (1990) and Inderlied (1991), see; Inderlied, C. B. (1991) as modified below were used to analyze the inhibitory effect of compounds of the invention on *Mycobacterium tuberculosis*. For specific methods of in vitro susceptibility testing, spectrums of activity, mechanisms of action and resistance, and assays for activity in biological fluids, see *Antibiotics in Laboratory Medicine*, Third Edition, edited by Victor Lorian, Williams and Wilkins, Baltimore, pp. 135–197; Jacobs, W. R. et al., "Genetic Systems for Mycobacteria," *Methods in Enzymology,* 204:537, 1991; and National Committee for Clinical Laboratory Standards (1990), Antimycobacterial susceptibility testing, Proposed standard M24-P, NCCLS, Villanova, Pa.

Preparation of Agar Plates: Middlebrook 7H10 agar medium (Difco) was prepared from a dehydrated base as recommended by the manufacturer. After autoclaving, the agar was allowed to cool to 50°–55° C. before adding filter-sterilized ADC enrichment (Jacobs et al., 1991). Test compounds prepared in accordance with the foregoing Examples, as listed by Example number in the following Table 1, and reference antibiotics (currently isoniazid) were resuspended in DMSO or sterile distilled water to obtain stocks ranging from 1 to 10 g/ml and were incorporated into the agar medium at appropriate concentrations. Approximately 5 mL of agar was dispensed into labeled quadrants of a series of sterile Petri dishes with one quadrant containing drug-free 7H10 medium. Plates were maintained at room temperature overnight.

Preparation of *M. tuberculosis* Inoculum: *M. tuberculosis* 10038 (Public Health Research Institute, New York, N.Y.) is a multidrug-resistant strain which has been shown to be 100% resistant to the front line antituberculosis agents isoniazid, rifampin, ethambutol and streptomycin, 90% resistant to kannamycin and 85% resistant to ethionamide. *M. tuberculosis* H37Rv (ATCC No. 27294) is a conventional drug sensitive strain. Colonies of *M. tuberculosis* H37Rv and *M. tuberculosis* 10038 were scraped from solid medium and transferred to a tube containing sterile saline. Contents of the tube were thoroughly homogenized using a vortex mixer and then allowed to stand for 30 minutes to allow particles and clumps to settle. The supernatant suspension was withdrawn and adjusted (visually or using a Klett-Summerson instrument) to a turbidity equivalent to a McFarland No. 1 standard. Cultures adjusted in this manner contained approximately $10^7$ colony forming units/mL.

Inoculation and Incubation of Plates: $10^{-2}$ and $10^{-4}$ dilutions of the standard *M. tuberculosis* suspension were prepared in sterile saline solution, 100 μl of which was inoculated onto each agar quadrant of two identical Petri dishes. After the inoculum dried, plates were sealed in polyethylene bags and transferred to a 37° C. incubator in an atmosphere of 5% carbon dioxide. Plates were examined each week for a period of four weeks. The lowest inhibitory concentration tested of the compounds tested is shown in Table 1, below, after three week incubation.

The in vitro inhibition of *Mycobacterium smegmatis* as shown in Table 1 was determined by the method of L. Mitscher et al., *J. Natural Products* 35:157, 1972.

TABLE 1

| | Lowest Inhibitory Concentration (μg/mL) of Indolo[2,1-b]quinazoline-6,12-dione Compounds Against Mycobacteria | | |
|---|---|---|---|
| Example | *Mycobacterium smegmatis* | *Mycobacterium tb.* MDR10038 | *Mycobacterium tb.* H37RV |
| tryptanthrin | 3.1 | 10 | 10 |
| 12 | 6.2 | <1 | <1 |
| 13 | 100 | <1 | <1 |
| 14 | >100 | 10 | >10 |
| 15 | >100 | 2 | nd |
| 16 | >100 | >10 | >10 |

TABLE 1-continued

| | Lowest Inhibitory Concentration (μg/mL) of Indolo[2,1-b]quinazoline-6,12-dione Compounds Against Mycobacteria | | |
|---|---|---|---|
| Example | *Mycobacterium smegmatis* | *Mycobacterium tb.* MDR10038 | *Mycobacterium tb.* H37RV |
| 17 | 1.5 | 1 | <0.2 |
| 18 | 3.1 | nd | nd |
| 19 | 0.8 | <1 | <1 |
| 20 | 1.5 | 1 | <0.2 |
| 21 | 100 | 1.0 | 1.0 |
| 22 | >100 | 5.0 | 5.0 |
| 23 | >100 | ≦0.2 | ≦0.2 |
| 24 | >100 | 1.0 | 1.0 |
| 25 | >100 | 2.0 | 2.0 |
| 26 | >100 | 5 | >5 |
| 27 | 0.8 | 1 | 1 |
| 28 | >100 | 1.3 | 1.3 |
| 29 | >100 | 1.3 | 1.3 |
| 30 | >100 | 5 | 5 |
| 31 | 100 | 1 | 1 |
| 32 | >100 | 1 | 1 |
| 33 | >100 | <0.3 | <0.3 |
| 34 | >100 | <0.3 | <0.3 |
| 35 | 100 | 1 | 1 |
| 36 | 0.8 | <0.5 | <0.5 |
| 37 | 1.5 | 1 | 1 |
| 38 | 50 | 5 | 5 |
| 39 | >100 | 1 | 1 |
| 40 | >100 | 5 | 5 |
| 41 | 1.5 | 1 | 1 |
| 42 | >100 | <0.4 | <0.4 |
| 43 | 1.5 | <0.4 | <0.4 |
| 45 | 25 | 5 | 5 |
| 46 | 25 | >5 | >5 |
| 47 | 25 | 5 | 5 |
| 48 | 25 | 1 | 1 |
| 49 | >100 | 10 | 10 |
| 50 | nd | >5 | >5 |
| 51 | nd | >5 | >5 |
| 52 | nd | >5 | >5 |
| 53 | nd | >5 | >5 |
| 54 | nd | 5 | >5 |
| 55 | 22 100 | 5 | 5 |
| 56 | 3.1 | 1 | 1 |
| 57 | 12.5 | <0.5 | <0.5 |
| 58 | >100 | 10 | 10 |

While the preferred embodiments of the invention have been illustrated and described, it will be appreciated that various changes can be made therein without departing from the spirit and scope of the invention.

The embodiments of the invention in which an exclusive property or privilege is claimed are defined as follows:

1. A compound of the formula:

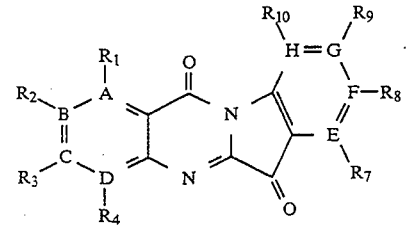

wherein A, B, C, D, E, F, G and H are independently selected from carbon and nitrogen, or A and B or C and D can be taken together to be nitrogen or sulfur, with the proviso that at least one of A, B, C, D, E, F, G and H must be other than carbon;

wherein $R_1$ through $R_4$, $R_8$ and $R_{10}$ are independently selected from the group consisting of hydrogen, halogen, loweralkyl, cycloalkyl, heterocycle, substituted heterocycle, amino, imino, haloloweralkyl, alkoxy, nitro, alkylsulfonyl, arylalkyl, arylalkylaryl, arylaryl, aryloxy, arylamino, acylamino, acyloxyamino, alkylaminoacylamino, alkylaminosulfonylamino, alkylamino, alkenylamino, dialkylamino, alkoxyalkylamino, mercaptoalkoxyalkyl, cyano, formyl, —COOR$_{11}$ where R$_{11}$ is hydrogen, loweralkyl, aryl, heterocycle, monosaccharide or disaccharide, and —COONR$_{12}$R$_{13}$ where R$_{12}$ and R$_{13}$ are independently selected from hydrogen, loweralkyl, aryl, heterocycle, saccharide, peptide and amino acid residues;

R$_7$ and R$_9$ are independently selected from hydrogen, halogen, loweralkyl, haloloweralkyl, cycloalkyl, heterocycle, substituted heterocycle and heterocyclicalkyl;

or R$_1$ through R$_{10}$ are absent when the ring atom to which they would otherwise be bonded is sulfur or double-bonded nitrogen;

and the pharmaceutically acceptable salts thereof.

2. A compound of claim 1 wherein D is N and R$_4$ is absent.

3. A compound of claim 2 wherein R$_1$ through R$_3$, R$_8$ and R$_{10}$ are independently selected from the group consisting of hydrogen, loweralkyl, heterocycle, substituted heterocycle, amino, halogen, nitro, alkylamino, dialkylamino, and alkoxyalkylamino;

R$_7$ and R$_9$ are independently selected from hydrogen, halogen, loweralkyl, cycloalkyl, heterocycle, substituted heterocycle and heterocyclicalkyl;

or a pharmaceutically acceptable salt thereof.

4. A compound of the formula (III):

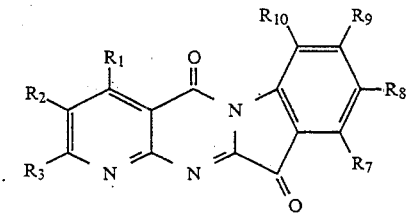

(III)

wherein R$_1$ through R$_3$, R$_8$ and R$_{10}$ are independently selected from the group consisting of hydrogen, loweralkyl, heterocycle, substituted heterocycle, amino, halogen, nitro, alkylamino, dialkylamino, alkoxyalkylamino, and alkylheterocycle;

R$_7$ and R$_9$ are independently selected from hydrogen, halogen, loweralkyl, cycloalkyl, heterocycle, substituted heterocycle and heterocyclicalkyl;

and the pharmaceutically acceptable salts thereof.

5. A compound of the formula (IV):

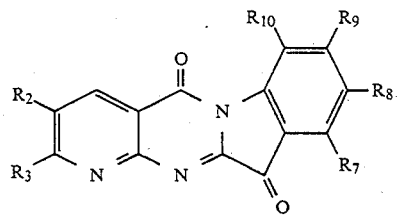

(IV)

wherein R$_2$, R$_3$, R$_8$ and R$_{10}$ are independently selected from the group consisting of hydrogen, halogen, loweralkyl, heterocycle, and substituted heterocycle;

R$_7$ and R$_9$ are independently selected from hydrogen and halogen;

and the pharmaceutically acceptable salts thereof.

6. A compound of claim 5 wherein R$_7$ and R$_9$ are hydrogen.

7. A compound of claim 5 wherein at least one of R$_2$, R$_3$, R$_8$ and R$_{10}$ is selected from the group consisting of halogen, loweralkyl, heterocycle, and substituted heterocycle.

8. A method of inhibiting the growth of pathogenic mycobacterium comprising contacting the mycobacterium with a growth inhibitory amount of an indolo[2,1-b]quinazoline-6,12-dione compound of the formula (I):

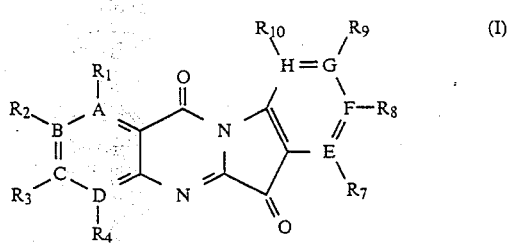

(I)

wherein A, B, C, D, E, F, G and H are independently selected from carbon and nitrogen, or A and B or C and D can be taken together to be nitrogen or sulfur, with the proviso that not more than three of A, B, C, D, E, F, G and H are other than carbon;

R$_1$ through R$_4$, R$_8$ and R$_{10}$ are independently selected from the group consisting of hydrogen, halogen, loweralkyl, cycloalkyl heterocycle, substituted heterocycle, amino, imino, haloloweralkyl, alkoxy, nitro, alkylsulfonyl, arylalkyl, arylalkylaryl, arylaryl, aryloxy, arylamino, acylamino, acyloxyamino, alkylaminoacylamino, alkylaminosulfonylamino, alkylamino, alkenylamino, dialkylamino, alkoxyalkylamino, alkoxyalkylheterocycle, mercaptoalkoxyalkyl, cyano, formyl, —COOR$_{11}$ where R$_{11}$ is hydrogen, loweralkyl, aryl, heterocycle, monosaccharide or disaccharide, and —COONR$_{12}$R$_{13}$ where R$_{12}$ and R$_{13}$ are independently selected from hydrogen, loweralkyl, aryl, heterocycle, saccharide, peptide and amino acid residues; and R$_7$ and R$_9$ are independently selected from hydrogen, halogen, loweralkyl, haloloweralkyl, cycloalkyl, heterocycle, substituted heterocycle and heterocyclicalkyl;

or R$_l$ through R$_{10}$ are absent when the ring atom to which they would otherwise be bonded is sulfur or double-bonded nitrogen;

or a pharmaceutically acceptable salt thereof.

9. The method of claim 8 wherein the indolo[2,1-b]quinazoline-6,12-dione is a compound of the formula (II):

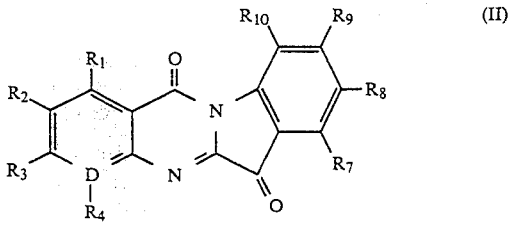

(II)

wherein D is carbon or nitrogen;

$R_1$ through $R_4$, $R_8$ and $R_{10}$ are independently selected from the group consisting of hydrogen, loweralkyl, heterocycle, substituted heterocycle, amino, halogen, nitro, alkylamino, dialkylamino, alkoxyalkylamino, and alkylheterocycle, provided that $R_4$ is absent when D is N; and $R_7$ and $R_9$ are independently selected from hydrogen, halogen, loweralkyl, cycloalkyl, heterocycle, substituted heterocycle and heterocyclicalkyl;

or a pharmaceutically acceptable salt thereof.

10. The method of claim 8 wherein the indolo[2,1-b]quinazoline-6,12-dione is a compound of the formula (III):

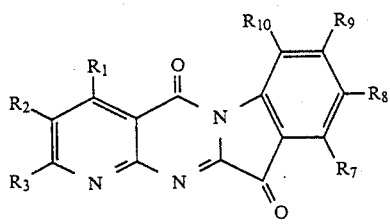

wherein $R_1$ through $R_3$, $R_8$ and $R_{10}$ are independently selected from the group consisting of hydrogen, loweralkyl, heterocycle, substituted heterocycle, amino, halogen, nitro, alkylamino, dialkylamino, alkoxyalkylamino, and alkylheterocycle;

$R_7$ and $R_9$ are independently selected from hydrogen, halogen, loweralkyl, cycloalkyl, heterocycle, substituted heterocycle and heterocyclicalkyl;

or a pharmaceutically acceptable salt thereof.

11. The method of claim 8 wherein the pathogenic mycobacterium is selected from the group consisting of *Mycobacteria tuberculosis*, *Mycobacteria leprae*, and *Mycobacteria avium* complex.

12. The method of claim 11 wherein the pathogenic mycobacterium is *Mycobacteria tuberculosis*.

13. The method of claim 12 wherein the pathogenic mycobacterium is a multidrug-resistant strain of *Mycobacteria tuberculosis*.

14. A method of treating a human or animal subject suffering from an infection by pathogenic mycobacteria comprising administering to the subject a therapeutically effective amount of a indolo[2,1-b]quinazoline-6,12-dione compound of formula (I):

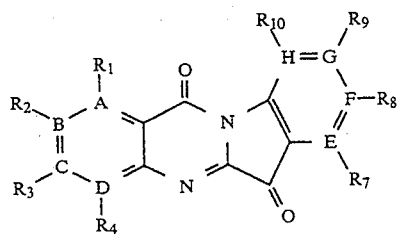

wherein A, B, C, D, E, F, G and H are independently selected from carbon and nitrogen, or A and B or C and D can be taken together to be nitrogen or sulfur, with the proviso that not more than three of A, B, C, D, E, F, G and H are other than carbon;

$R_1$ through $R_4$, $R_8$ and $R_{10}$ are independently selected from the group consisting of hydrogen, halogen, loweralkyl, cycloalkyl, heterocycle, substituted heterocycle, amino, imino, haloloweralkyl, alkoxy, nitro, alkylsulfonyl, arylalkyl, arylalkylaryl, arylaryl, aryloxy, arylamino, acylamino, acyloxyamino, alkylaminoacylamino, alkylaminosulfonylamino, alkylamino, alkenylamino, dialkylamino, alkoxyalkylamino, alkoxyalkylheterocycle, mercapyalkylamino, alkoxyalkylheterocycle, mercaptoalkoxyalkyl, cyano, formyl, $-COOR_{11}$ where $R_{11}$ is hydrogen, loweralkyl, aryl, heterocycle, monosaccharide or disaccharide, and $-COONR_{12}R_{13}$ where $R_{12}$ and $R_{13}$ are independently selected from hydrogen, loweralkyl, aryl, heterocycle, saccharide, peptide and amino acid residues; and $R_7$ and $R_9$ are independently selected from hydrogen, halogen, loweralkyl, haloloweralkyl, cycloalkyl, heterocycle, substituted heterocycle and heterocyclicalkyl;

or $R_1$ through $R_{10}$ are absent when the ring atom to which they would otherwise be bonded is sulfur or double-bonded nitrogen;

or a pharmaceutically acceptable salt thereof;

alone or together with a pharmaceutically acceptable carrier.

15. The method of claim 14 wherein the indolo[2,1-b]quinazoline-6,12-dione is a compound of the formula (II):

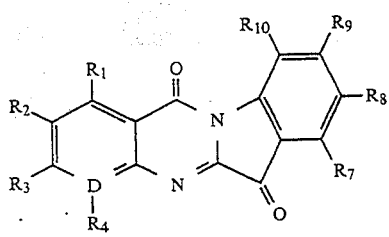

wherein D is carbon or nitrogen;

$R_1$ through $R_4$, $R_8$ and $R_{10}$ are independently selected from the group consisting of hydrogen, loweralkyl, heterocycle, substituted heterocycle, amino, halogen, nitro, alkylamino, dialkylamino, alkoxyalkylamino, and alkylheterocycle, provided that $R_4$ is absent when D is N; and $R_7$ and $R_9$ are independently selected from hydrogen, halogen, loweralkyl, cycloalkyl, heterocycle, substituted heterocycle and heterocyclicalkyl;

or a pharmaceutically acceptable salt thereof.

16. The method of claim 14 wherein the indolo[2,1-b]quinazoline-6,12-dione is a compound of the formula (III):

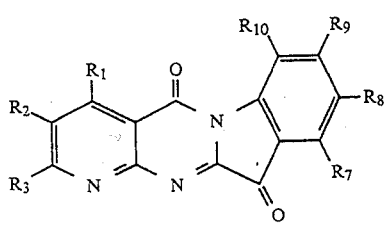

wherein $R_1$ through $R_3$, $R_8$ and $R_{10}$ are independently selected from the group consisting of hydrogen, loweralkyl, heterocycle, substituted heterocycle, amino, halogen, nitro, alkylamino, dialkylamino, alkoxyalkylamino, and alkylheterocycle; and $R_7$ and $R_9$ are independently selected from hydrogen, halogen, loweralkyl, cycloalkyl, heterocycle, substituted heterocycle and heterocyclicalkyl;

or a pharmaceutically acceptable salt thereof.

17. The method of claim 14 wherein the human or animal subject is suffering from infection by pathogenic mycobacteria selected from the group consisting of *Mycobacteria tuberculosis, Mycobacteria leprae,* and *Mycobacteria avium* complex.

18. The method of claim 17 wherein the pathogenic mycobacterium is *Mycobacteria tuberculosis.*

19. The method of claim 17 wherein the pathogenic mycobacterium is a multidrug-resistant strain of *Mycobacteria tuberculosis.*

* * * * *

UNITED STATES PATENT AND TRADEMARK OFFICE
CERTIFICATE OF CORRECTION

| | | |
|---|---|---|
| PATENT NO. : | 5,441,955 | Page 1 of 3 |
| DATED : | August 15, 1995 | |
| INVENTOR(S) : | W.R. Baker et al. | |

It is certified that error appears in the above-indentified patent and that said Letters Patent is hereby corrected as shown below:

On the title page, item

| | | |
|---|---|---|
| [54]<br>(pg. 1, col. 1) | Title | "INDOLO[2,1-BIQUINAZOLINE-6,12-DIONE" should read --INDOLO[2,1-b]QUINAZOLINE-6,12-DIONE-- |
| 1 | 1 | "INDOLO[2,1-BIQUINAZOLINE-6,12-DIONE" should read --INDOLO[2,1-b]QUINAZOLINE-6,12-DIONE-- |
| [56]<br>(pg. 1, col. 1) | Refs. Cited<br>Other Pubs. | "Quinazolin" should read --Quinazoline-- |
| [56]<br>(pg. 1, col. 1) | Refs. Cited<br>Other Pubs. | "*Guianesis*" should read --*Guianensis*-- |
| [57]<br>(pg. 1, col. 2) | Abstract<br>(line 2) | "form" should read --for-- |
| [56]<br>(pg. 2, col. 2) | Refs. Cited<br>Other Pubs. | "85563c," should read --8563c,-- |
| Column | Line | |
| 7 | 32 | "maybe" should read --may be-- |
| 7 | 34 | "maybe" should read --may be-- |
| 13 | 27-28 | after "addition" insert --to--. |

UNITED STATES PATENT AND TRADEMARK OFFICE
CERTIFICATE OF CORRECTION

PATENT NO. : 5,441,955  
DATED : August 15, 1995  
INVENTOR(S) : W.R. Baker et al.

Page 2 of 3

It is certified that error appears in the above-indentified patent and that said Letters Patent is hereby corrected as shown below:

COLUMN          LINE 30          25          "at at" should read --at--

44          63          "chromatorgraphy" should read --chromatography--

46          46          "
(Example 95)

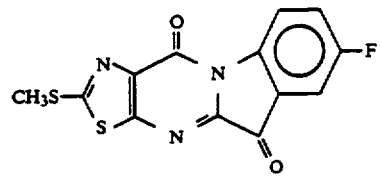

"

should read

—

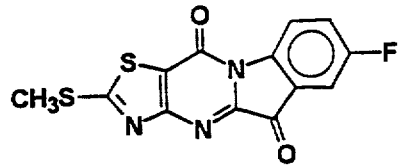

—

UNITED STATES PATENT AND TRADEMARK OFFICE
CERTIFICATE OF CORRECTION

PATENT NO. : 5,441,955
DATED : August 15, 1995
INVENTOR(S) : W.R. Baker, et al

It is certified that error appears in the above-indentified patent and that said Letters Patent is hereby corrected as shown below:

| Column | Line | |
|---|---|---|
| 48 (Table 1) | 38 | "22 100" should read -->100-- |

Signed and Sealed this

Ninth Day of January, 1996

Attest:

BRUCE LEHMAN

Attesting Officer

Commissioner of Patents and Trademarks